(12) United States Patent
Brown et al.

(10) Patent No.: US 9,465,000 B1
(45) Date of Patent: Oct. 11, 2016

(54) SYSTEM AND METHOD FOR ELECTRONICALLY DETERMINING FLUID PARAMETERS

(71) Applicant: Intellectual Reserves, LLC, Parker, TX (US)

(72) Inventors: Leon Brown, Parker, TX (US); Alvin R Wirthlin, Allen, TX (US)

(73) Assignee: Intellectual Reserves, LLC, Allen, TX (US)

( * ) Notice: Subject to any disclaimer, the term of this patent is extended or adjusted under 35 U.S.C. 154(b) by 0 days.

(21) Appl. No.: 14/829,209

(22) Filed: Aug. 18, 2015

(51) Int. Cl.
*G01N 27/02* (2006.01)

(52) U.S. Cl.
CPC .................................. *G01N 27/02* (2013.01)

(58) Field of Classification Search
None
See application file for complete search history.

(56) References Cited

U.S. PATENT DOCUMENTS

| | | | |
|---|---|---|---|
| 7,339,657 B2 | 3/2008 | Coates | |
| 7,651,262 B2 | 1/2010 | Nishina et al. | |
| 7,954,312 B2 | 6/2011 | Gresens | |
| 8,293,180 B2 | 10/2012 | Matsunaga et al. | |
| 2004/0218000 A1* | 11/2004 | Farr | B41J 2/17566 347/19 |
| 2005/0011183 A1 | 1/2005 | Ripper et al. | |
| 2005/0118705 A1* | 6/2005 | Rabbitt | B01L 3/502761 435/287.1 |
| 2006/0214671 A1* | 9/2006 | Wooton | G01N 27/026 324/698 |
| 2008/0143345 A1 | 6/2008 | Boudaoud et al. | |
| 2010/0327884 A1 | 12/2010 | McCall et al. | |
| 2011/0036861 A1 | 2/2011 | Hillel et al. | |
| 2012/0068723 A1* | 3/2012 | Sullivan | G01N 27/07 324/654 |
| 2013/0074590 A1 | 3/2013 | Bertow et al. | |
| 2014/0152332 A1* | 6/2014 | Platte | G01N 27/07 324/713 |
| 2014/0368823 A1* | 12/2014 | Wirthlin | G01N 21/43 356/448 |
| 2015/0226683 A1* | 8/2015 | Feldman | A01J 5/0133 324/640 |
| 2016/0018347 A1* | 1/2016 | Drbal | A61M 1/28 210/647 |

FOREIGN PATENT DOCUMENTS

| | | |
|---|---|---|
| DE | 19706486 A1 | 8/1998 |
| WO | 2009065721 A1 | 5/2009 |
| WO | 2011078629 A1 | 6/2011 |
| WO | 2013010625 A1 | 1/2013 |
| WO | 2013030067 A1 | 3/2013 |

* cited by examiner

*Primary Examiner* — Jermele M Hollington
(74) *Attorney, Agent, or Firm* — Alvin R. Wirthlin

(57) ABSTRACT

A system and method for measuring at least one property of a fluid includes a housing for receiving the fluid, a first and second spaced electrodes positioned in the housing, and an impedance modifier positioned between the first and second electrodes that changes an electrical impedance of the fluid between the electrodes. Electronic circuitry generates different waveform voltages across the electrodes and the fluid, monitors an output thereof to thereby obtain data related to impedance of the fluid for each waveform voltage; and combines data related to the outputs to create a unique identification signature for the fluid. Once signatures for known fluids have been created, they can be compared to a generated signature of an unknown fluid to identify the unknown fluid.

23 Claims, 24 Drawing Sheets

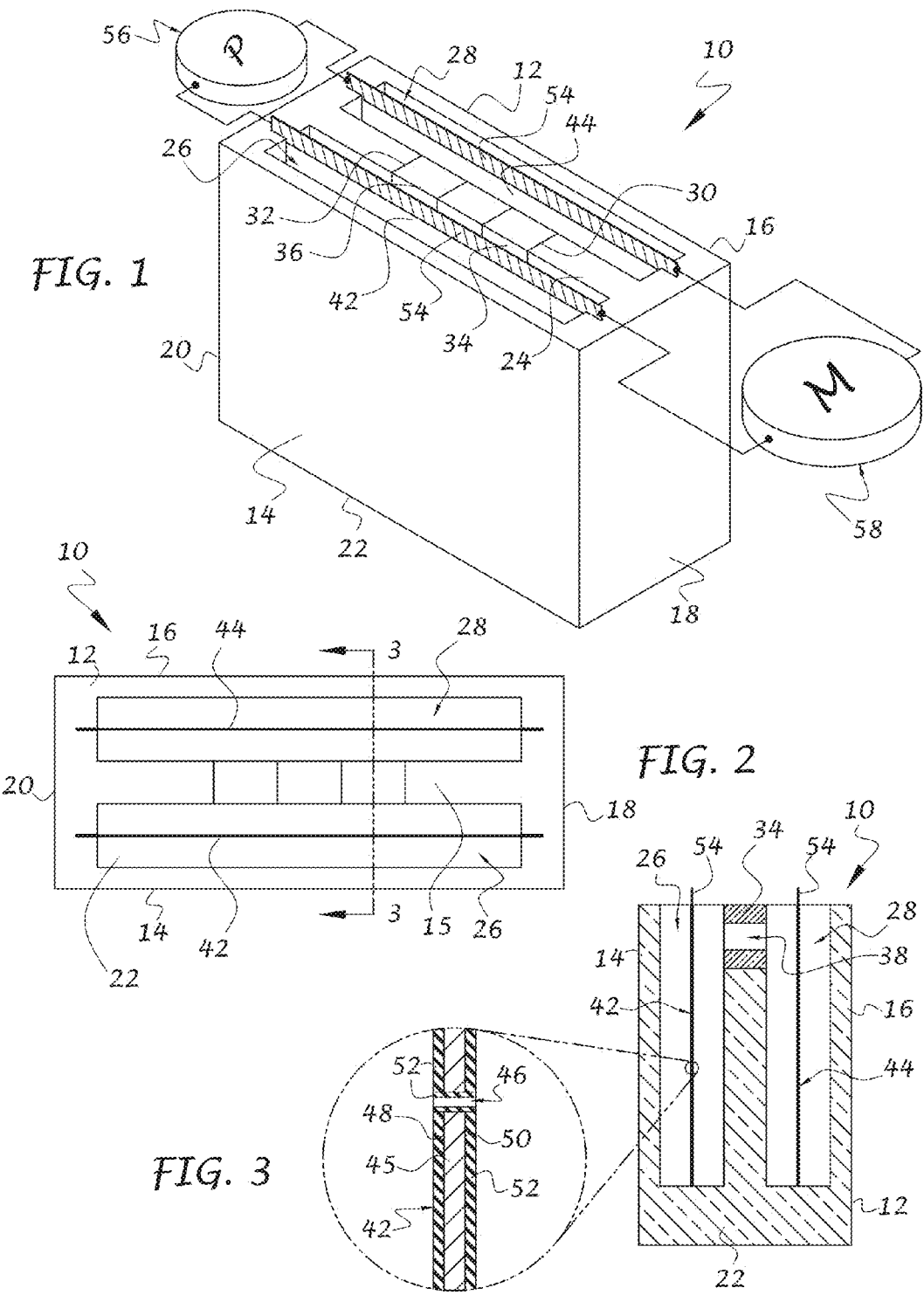

DEF Capacitance & Resistance vs Frequency

| FREQ (Hz) | | C (nF) | R (Ohm) |
|---|---|---|---|
| 20 | | 1,090 | 18.95k |
| 50 | | 504.4 | 14.61k |
| 100 | | 295.5 | 12.05k |
| 500 | | 82.79 | 7.699k |
| 1,000 | | 49.45 | 6.206k |
| 2,000 | | 30.147 | 5.008k |
| 5,000 | | 14.605 | 3.826k |
| 10,000 | (10KHz) | 7.604 | 2.954k |
| 20,000 | | 4.639 | 1.945k |
| 50,000 | | 4.064 | 1.945k |
| 100,000 | (100KHz) | 1.853 | 328 |
| 200,000 | | 1.672 | 147 |
| 500,000 | | 1.537 | 75 |
| 1,000,000 | (1MHz) | 1.434 | 58 |

SYSTEM AND METHOD FOR ELECTRONICALLY DETERMINING FLUID PARAMETERS

BACKGROUND OF THE INVENTION

This invention relates to measurement devices, and more particularly to a system and method for electronically determining fluid quality, fluid composition, and other fluid parameters.

Transducers for measuring liquid level and other parameters are often used in the transportation industry including heavy duty trucks and light duty vehicles, as well as the off-road industry including farm and construction equipment, and other industries such as industrial equipment including power generators, as well as other industries, systems and machines. The electrical output of such transducers change in response to a change in the liquid being measured, and is typically in the form of a change in resistance, capacitance, current flow, magnetic field, frequency, and so on. These types of transducers may include variable capacitors or resistors, optical components, Hall Effect sensors, strain gauges, ultrasonic devices, tuning forks, and so on.

In vehicles, heavy duty trucks, off-road equipment, industrial equipment and other systems and machines powered by diesel fuel, a Selective Catalytic Reduction (SCR) system has been used to inject urea, a liquid-reductant agent, through a catalyst into the exhaust stream of a diesel engine. Urea sets off a chemical reaction that converts nitrogen oxides in the exhaust into nitrogen and water, which is then harmlessly expelled through the vehicle tailpipe into the atmosphere.

Previous urea quality sensor solutions have attempted to address industry quality control by ensuring that a specific quality of urea can be delivered into the exhaust gas stream. If the engine is operated without urea solution in the onboard urea tank, excessive NOx emissions can occur. Using a urea quality sensor, the SCR system can monitor the contents of the urea tank to alert an operator and/or system that the urea tank has been filled with other fluids, e.g., with tap water, coolant, windshield wiper fluid, oil, incorrect concentrations of urea solutions, and so on, instead of the correct concentration of urea solution. The introduction of a urea quality sensor into the SCR system also reduces the risk of tampering or accidental mis-filling and helps ensure compliance to environmental legislation, thus satisfying concerns of users and legislators alike. The urea quality sensor is intended to contribute to the overall success of SCR as a NOx reduction technology. However, prior art solutions for measuring the presence or absence of the required urea concentration, such as refractive index measurements, capacitive, acoustic, tuning fork, and other known techniques, have been unable to measure the urea concentration with any degree of suitable accuracy to meet rigid industry and legislative requirements.

It would therefore be desirous to provide a system and method for determining the quality of fluids and other parameters with a higher degree of accuracy than prior art systems and methods in order to quantify whether or not proper fluid and/or the proper concentrations of fluids are being used in vehicles, machinery, and so on. It would also be desirous to provide a system and method for identifying the fluid being measured and the purity of such fluid, including the contents of a particular fluid mixture.

BRIEF SUMMARY OF THE INVENTION

According to one aspect of the invention, a system for measuring at least one property of a fluid includes a housing for receiving the fluid, a first and second spaced electrodes positioned in the housing, and an impedance modifier positioned between the first and second electrodes. The impedance modifier includes at least one opening or conduit with a predetermined diameter or cross-dimension and a predetermined length to define a restricted flow volume so that fluid flowing between the first and second electrodes passes only through the impedance modifier to thereby increase an electrical impedance of the fluid between the electrodes. Electronic circuitry is operably associated with the first and second electrodes for generating signals across the electrodes and the fluid located between the electrodes, and analyzing resulting signals to determine the one or more properties of the fluid.

According to a further aspect of the invention, a method for measuring at least one property of a fluid includes: providing first and second conductive electrodes at a predetermined distance; at least partially immersing the electrodes in a fluid to be measured; generating a plurality of different waveform voltages across the first and second electrodes and the fluid; monitoring an output to thereby obtain data related to a conductivity of the fluid for each waveform voltage; and combining data related to the output to create a unique identification signature for the fluid.

According to a further aspect of the invention, the method further includes providing waveform voltages in the form of sinusoidal waveforms at different frequencies.

According to yet a further aspect of the invention, the method further includes generating and storing a plurality of different unique identification signatures associated with a plurality of different known fluids; generating a unique identification signature for an unknown fluid; and identifying the unknown fluid by comparing the unique identification signature of the unknown fluid with one or more unique identification signatures of the known fluids.

BRIEF DESCRIPTION OF THE DRAWINGS

The foregoing summary as well as the following detailed description of the preferred embodiments of the present invention will be best understood when considered in conjunction with the accompanying drawings, wherein:

FIG. 1 is an isometric view of an exemplary measurement system for determining the fluid quality and other parameters in accordance with the present invention;

FIG. 2 is a top plan view of view of a fluid measurement cell in accordance with one exemplary embodiment of the invention that forms part of the measurement system of FIG. 1 and showing installed impedance modifiers;

FIG. 3 is a sectional view of the fluid measurement cell taken along line 3-3 of FIG. 2 with an enlarged portion showing the details of a measurement electrode;

FIG. 10 shows a first chart representing raw electrical characteristic data gathered for a particular fluid being measured upon application of a range of frequencies to the fluid in accordance with an exemplary signal generating and data gathering method of the invention;

Figure 4:
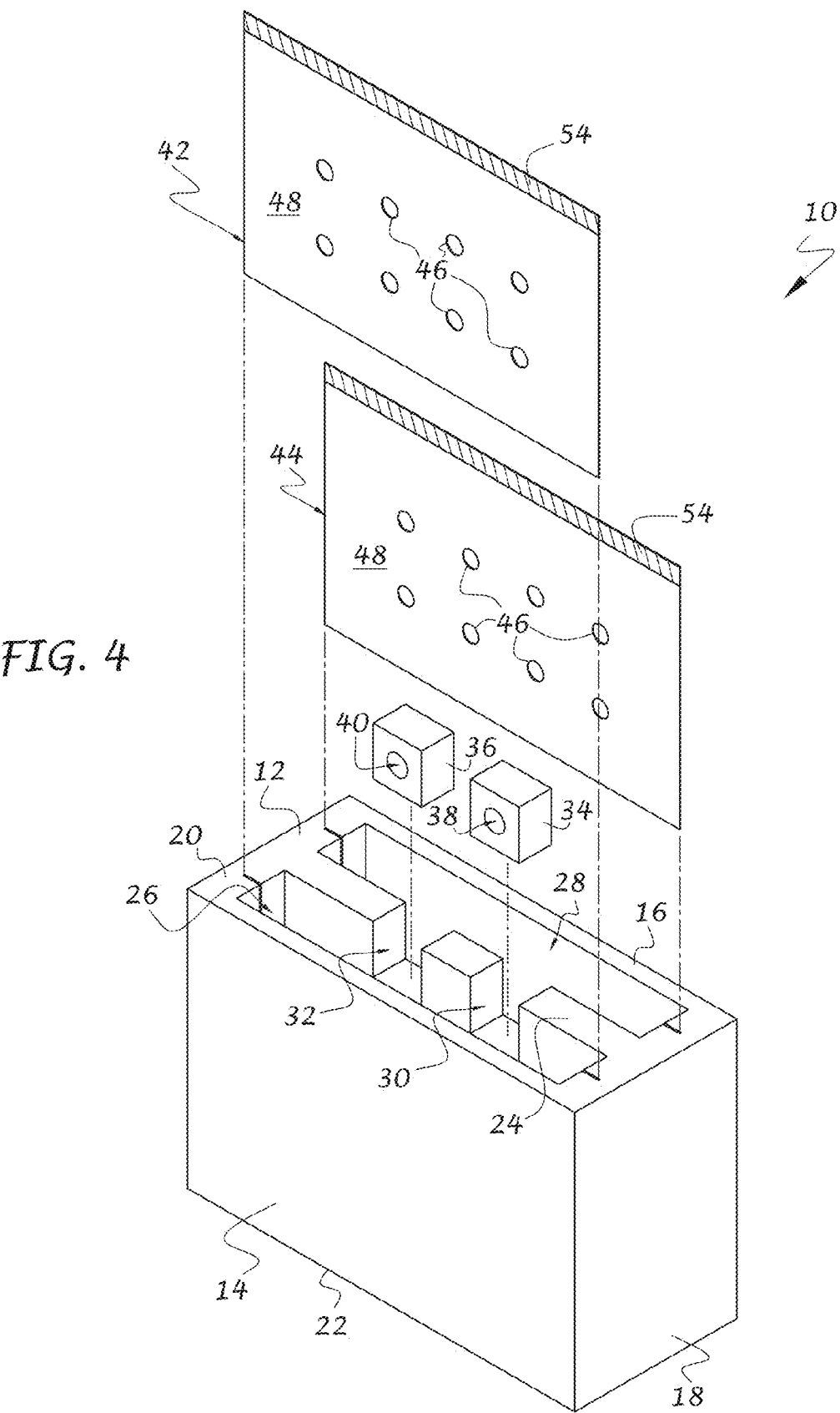
FIG. 4 is an isometric exploded view of the fluid measurement cell of FIG. 2.
Figure 5:
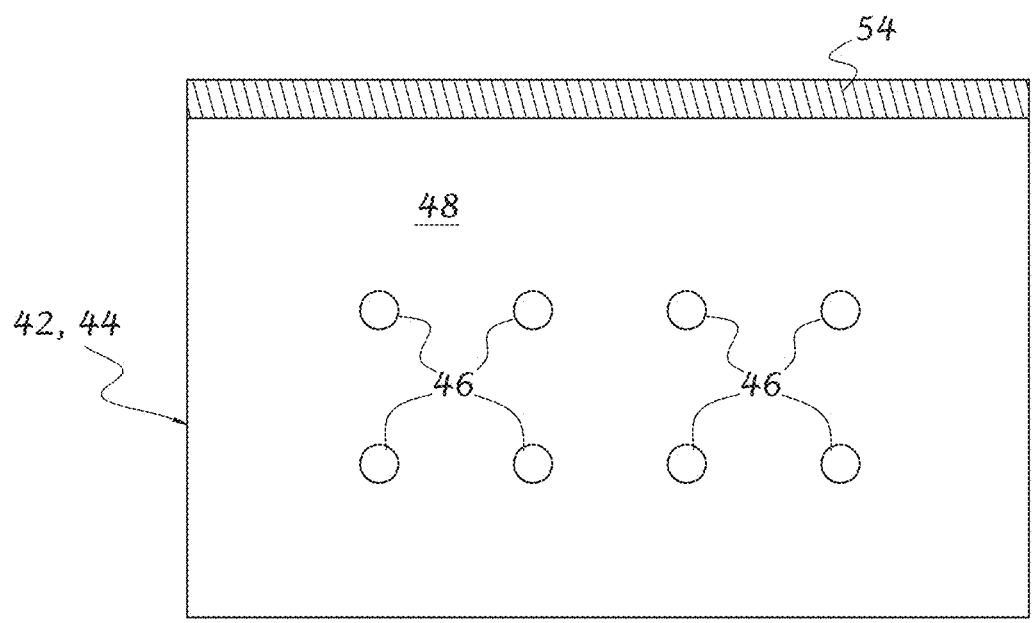
FIG. 5 is a front elevational view of an electrode that forms part of the measurement cell of FIG. 2.

It is noted that the drawings are intended to depict only typical or exemplary embodiments of the invention and therefore should not be considered as limiting the scope thereof. It is further noted that the drawings are not necessarily to scale. The invention will now be described in greater detail with reference to the accompanying drawings, wherein like designations denote like elements throughout the drawings.

DETAILED DESCRIPTION OF THE INVENTION

Referring to the drawings, and to FIG. 1 in particular, an exemplary fluid measurement system 10 in accordance with the invention for determining the composition, content, quality, and/or other parameters of a fluid or liquid is illustrated. Parameters that can be measured by the invention include, but are not limited to, the purity of a liquid or solution, the percentage or ratio(s) of different fluids and/or solids within different solutions, the determination of substitute fluids and/or solids mixed into the system to obtain lower cost solutions that may be detrimental to the machinery or systems associated with the fluid, the particular composition of the fluid, and so on.

The invention is described herein with an emphasis on methods for measuring and determining the authenticity, purity, concentration level, and age of diesel exhaust fluid (DEF), as well as various contaminants that may be found or introduced into the DEF, e.g. the composition of the fluid and/or other fluids that may be mixed in with the DEF or substituted therefor, and introduced into a DEF tank or SCR system or the like. However, it will be understood that the principles, exemplary measurement and determination techniques, as well as the various systems, components, and assemblies of the present invention, can be applied to the measurement and determination of various parameters of many other fluids and/or solutions, including the quality and composition thereof, without departing from the spirit and scope of the invention.

The exemplary fluid measurement system 10 of the present invention is intended to illustrate the principles discovered and employed in the present invention and has been used primarily for gathering various data of fluid(s) located in the system 10 as reflected in in the charts shown in FIGS. 9-20. However, it will be understood that such principles can be embodied in other measurement systems described herein, as well as their equivalents in principle, for achieving similar results albeit of varying signal magnitudes. Accordingly, the particular embodiments shown and described by way of example herein are intended to illustrate certain common principles within the various structures that can be used for measuring the fluid of interest and the data gathering techniques of the invention as described herein.

Figure 6:
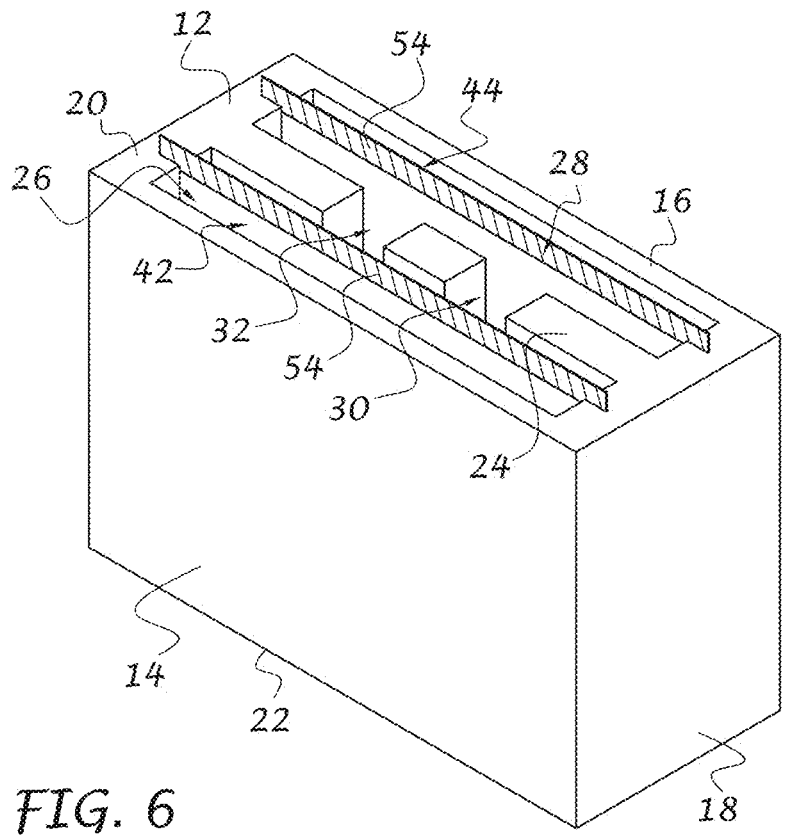
FIG. 6 is an isometric view of the measurement cell of FIG. 2 with the impedance modifiers removed.

Thus, as shown in FIGS. 1-6, the exemplary measurement system 10 of the invention preferably includes a measurement cell or housing 12 with a front wall 14, a rear wall 16 spaced from and extending parallel to the front wall 14, a left side wall 18 and a right side wall 20 extending between the front and rear walls, and a bottom wall 22 that connects the front, rear, left and right side walls. A middle divider wall section 24 extends from the bottom wall 22 and between the left and right side walls 18 and 20, respectively, and divides the measurement cell 12 into a first hollow compartment or chamber 26 and a second hollow compartment or chamber 28 on opposite sides of the middle wall section 24 for receiving liquid 25 (FIG. 7) to be measured. The first and second compartments 26, 28 are fluidly connected via one or more openings or restricted flow volumes 30, 32 formed in the middle wall section 24. Each opening 30, 32 forms a restricted flow space or volume for a purpose to be described in greater detail below. As best shown in FIG. 4, the openings 30, 32 can receive one or more electrically insulative impedance modifiers 34, 36 with smaller restricted flow spaces or volumes 38, 40, respectively. It will be understood that the impedance modifiers can be eliminated, as shown in FIG. 6, and that the restricted flow spaces or volumes can be formed directly in the housing 12 between the compartments 26, 28 without departing from the spirit and scope of the invention. It will be further understood that the restrictive flow volumes can be formed anywhere on the wall that separates the compartments, as will be described with reference to further embodiments below.

As best shown in FIGS. 3 and 4, a first electrode 42 is located in the first compartment 26, preferably centered between the front wall 14 and the middle wall section 24, so that the liquid to be measured is located on both sides of the first electrode. Likewise, a second electrode 44 is located in the second compartment 28, preferably centered between the rear wall 16 and the middle wall section 24, so that the liquid to be measured is also located on both sides of the second electrode 44. Each electrode 42, 44 preferably includes a conductive plate or element 45 (FIG. 3) with holes 46 (FIGS. 4 and 5) formed therein to allow fluid within the compartments 26, 28 to flow through the electrodes and expose opposing surfaces 48, 50 thereof so that the fluid within the compartments 26, 28 can flow through the electrodes 42, 44 respectively, to thereby maximize the surface area of the electrodes in a minimum amount of space. Each conductive plate 45 is preferably coated with an electrically nonconductive layer 52 on opposing sides thereof and through the holes 46 so that the conductive plate 45 is isolated from the liquid within the compartments. In this manner, corrosion of the electrodes as well as their consequent electrical signal degradation are substantially reduced or eliminated. Insulative materials that may be suitable for the non-conductive layer 52 can include but are not limited to, Parylene™ or other poly(p-xylylene) polymer, fluoropolymers, plastics, elastomers, enamels, ceramics, and so on, and that such materials may be applied using different techniques, such as painting, powder coating, dipping, vapor deposition, and so on, in different thicknesses depending on the particular liquid to be measured. Moreover, some non-conductive materials may be more suitable than others for certain liquids to be measured. For automotive-type liquids, including DEF, antifreeze, windshield washer fluid, oil, and the like, it has been found that a thin coating, such as 0.5 to 1 Mil thickness of Parylene™ or other chemical vapor deposited poly(p-xylylene) polymers, is an especially suitable insulative layer for the liquid quality measurements that will be described in greater detail below. However, it will be understood that other materials and/or material thickness can be used for the insulative layers without departing from the spirit and scope of the invention.

It will be further understood that in some instances the insulative layers may be eliminated, such as when the liquid is substantially non-conductive or when the electrodes are operatively associated with other components, such as a sacrificial anode, that is intended to bear the brunt of any potential galvanic corrosion, thereby reducing or eliminating degradation of the electrodes and thus subsequent degradation in the measurement of the liquid under consideration.

In accordance with a further embodiment of the invention, it will be understood that the insulative layers, when used, can be partially conductive, e.g. the layers need not be a perfect insulator, since the measurement techniques of the invention are capable of differentiating different fluids, as will be demonstrated below.

Each electrode 42, 44 preferably has an exposed conductive area 54 (best shown in FIGS. 4 and 5) above the height of the liquid level or at any other position isolated from the liquid, for connection to an electrical power source 56 and an electrical measurement device 58 (FIGS. 1, 7, and 7A) to thereby determine the composition, quality, and other parameters of the liquid being measured. Although the holes 46 are shown with a particular size, number, and pattern, it will be understood that these features can greatly vary without departing from the spirit and scope of the invention. It will also be understood that the holes can be eliminated and features in the housing 12 can be modified to include holes or passages to ensure that the liquid is present on both sides of the electrodes. Moreover, where space permits, or when the surface area of the electrodes is large enough on one side to obtain the desired readings, the holes can be eliminated so that only one face of one or both electrodes is exposed to the liquid to be measured.

Figure 7:
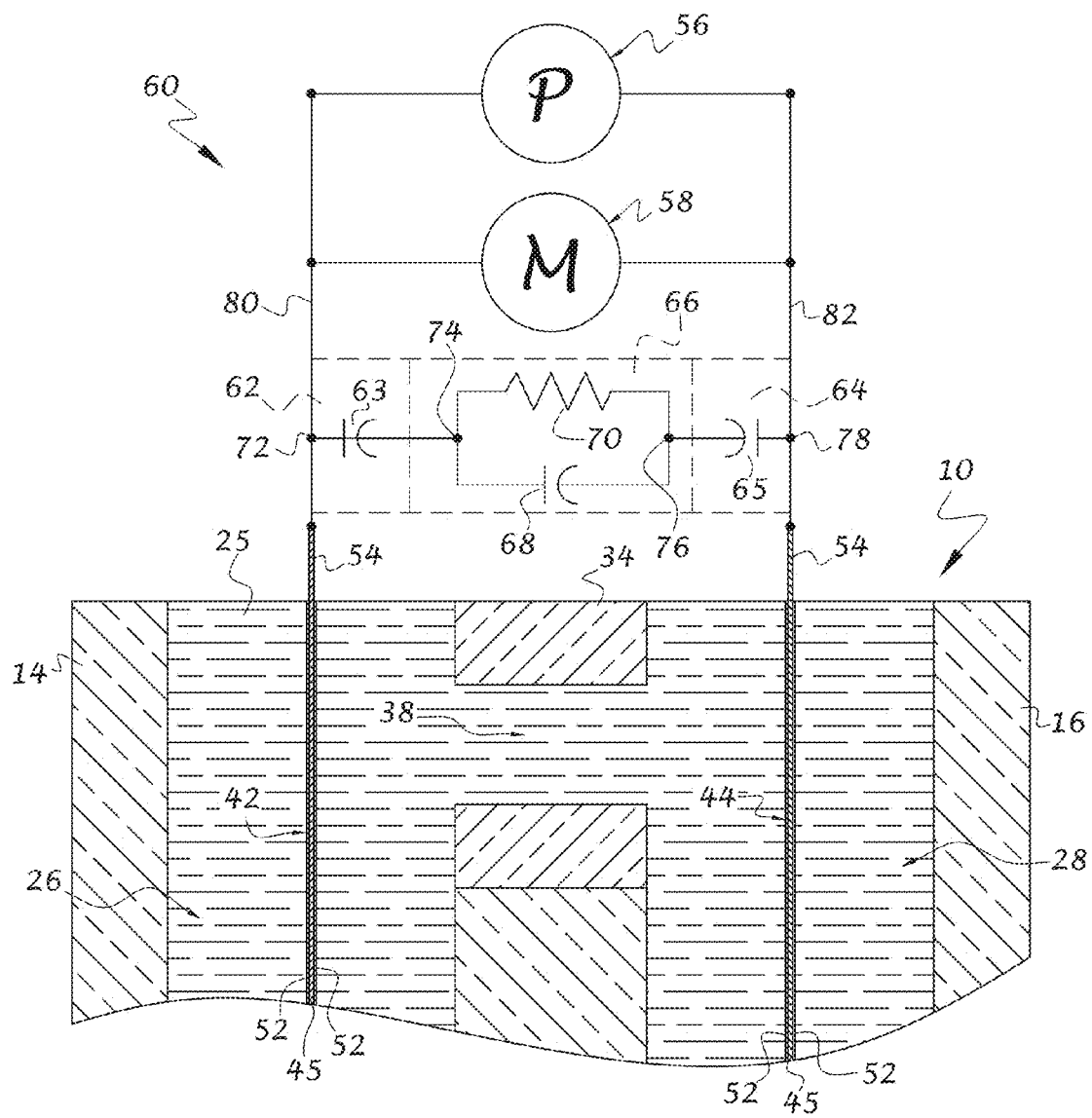
FIG. 7 is a schematic view of equivalent electrical circuitry of the measurement system of FIG. 1 with equivalent electrical devices representing the electrodes and fluid located within the measurement cell, with a meter or the like positioned in parallel with the components for measuring impedance or a voltage component of the impedance of the system, including the fluid being measured in the measurement cell.

Referring now to FIG. 7, an equivalent electrical circuit 60 of the measurement system 10 of FIG. 1 is schematically shown. The electrical circuit 60 includes a first electrical device 62 having a first capacitor 63 defined by the conductive plate 45 of the first electrode 42, the insulative layer 52 surrounding the conductive plate, and the fluid 25 in contact with the insulative layer 52 within the first compartment 26. Likewise, the electrical circuit 60 includes a second electrical device 64 having a second capacitor 65 defined by the conductive plate 45 of the second electrode 44, the insulative layer 52 surrounding the conductive plate, and the fluid 25 in contact with the insulative layer 52 in the second compartment 28.

A third electrical device 66 of the electrical circuit 60 is defined by the liquid 25 itself, and is in series with the first electrical device 62 and second electrical device 64. The third electrical device 66 includes a third capacitor 68 in parallel with a first resistor 70, which are in series with the first capacitor 63 and second capacitor 65. The first, second, and third electrical devices define the impedance of the measuring system, which can be measured by the meter 58, which, as shown in FIG. 7, is in parallel with the equivalent electrical circuit 60. It will be understood that the impedance can be measured between any two or more points 72, 74, 76, and/or 78 for example, for obtaining the impedance and/or a portion thereof of the circuit 60 by providing two or more insulated electrical traces between the two or more points and the meter 58. The electrical traces can comprise conductive traces formed on a printed circuit board (PCB), insulated wires, ribbons, conductive tabs, and so on. For purposes of discussion, the equivalent electrical circuit 60 is shown somewhat simplified since the insulator and fluid on each side of the conductive plate could form two separate capacitors in series for example. Also, depending on the material used for insulating the electrodes or the absence of material, as well as the properties of the liquid being measured, the equivalent electrical circuit can include one or more inductors and/or resistors in series and/or in parallel, as well as capacitors in series and/or in parallel, as well as other equivalent electronic devices. For example, the fluid under consideration may be represented as a variable capacitor in series with a variable resistor rather than in parallel. Moreover, the impedance of the liquid being measured can greatly change depending on several factors such as the dielectric constant of the liquid or the change in dielectric constant, including whether the fluid being measured is more conductive or insulative, whether there are contaminants or other components that change the conductivity or capacitance of the fluid, the temperature of the fluid, as well as the size or surface area of the electrodes exposed to the liquid and the thickness of the insulative layers.

In order to minimize the effects of the capacitors 63 and 65 on the impedance measurement of the liquid, the surface areas of the conductive plates are made as large as physically possible, given the size constraints for practical implementation of the invention, and the insulative coating is made as thin as practically possible without sacrificing consistency in measurement, e.g. the insulative film or coating is sufficiently thick to ensure the absence of pin holes or areas where the insulative film may not sufficiently cover the electrode. Exemplary embodiments of the invention with conductive plates having maximized surface areas over a minimal volume or footprint will be discussed in greater detail below. With the provision of conductive plates having relatively large surface areas (including the front and rear surfaces of such plates), together with very thin insulative coatings deposited on the conductive plates, it has been discovered that the capacitor components 63 and 65 associated with the plates are so small in relation to the impedance measurements of the fluid that they can be removed from the equation without significantly affecting measurement accuracy.

Moreover, the provision of one or more reduced flow volumes or spaces 38 between the electrodes 42 and 44 with a relatively small diameter or cross section, together with a relatively long length or thickness of the flow volume, forces the electrons in the liquid to funnel through the reduced flow volumes, which greatly increases the impedance of the fluid through such restricted flow volumes, thereby further eliminating the impedance created by the plates and insulative coatings. In this manner, changes in impedance due to structural changes of the measurement cell under changing environmental conditions can be minimized or eliminated, and therefore will not affect the impedance readings of the liquid being measured under changing environmental conditions.

In addition, the increased impedance of the fluid due to one or more of the restricted flow volumes permits a wider measuring range of the fluid under consideration, and thus increases the accuracy of the fluid measurement system 10. With the provision of increased impedance measurement of the fluid in accordance with the invention, care should be taken when designing the reduced flow volume(s) so that the impedance value of the liquid does not exceed a level that becomes impractical to measure. For example, it may be more practical to measure impedance of the fluid in the kilo-ohm range than in the Mega-ohm range. However, it will be understood that all ranges are well within the purview of the invention, even though some ranges may be less practical than others.

Figure 7A:
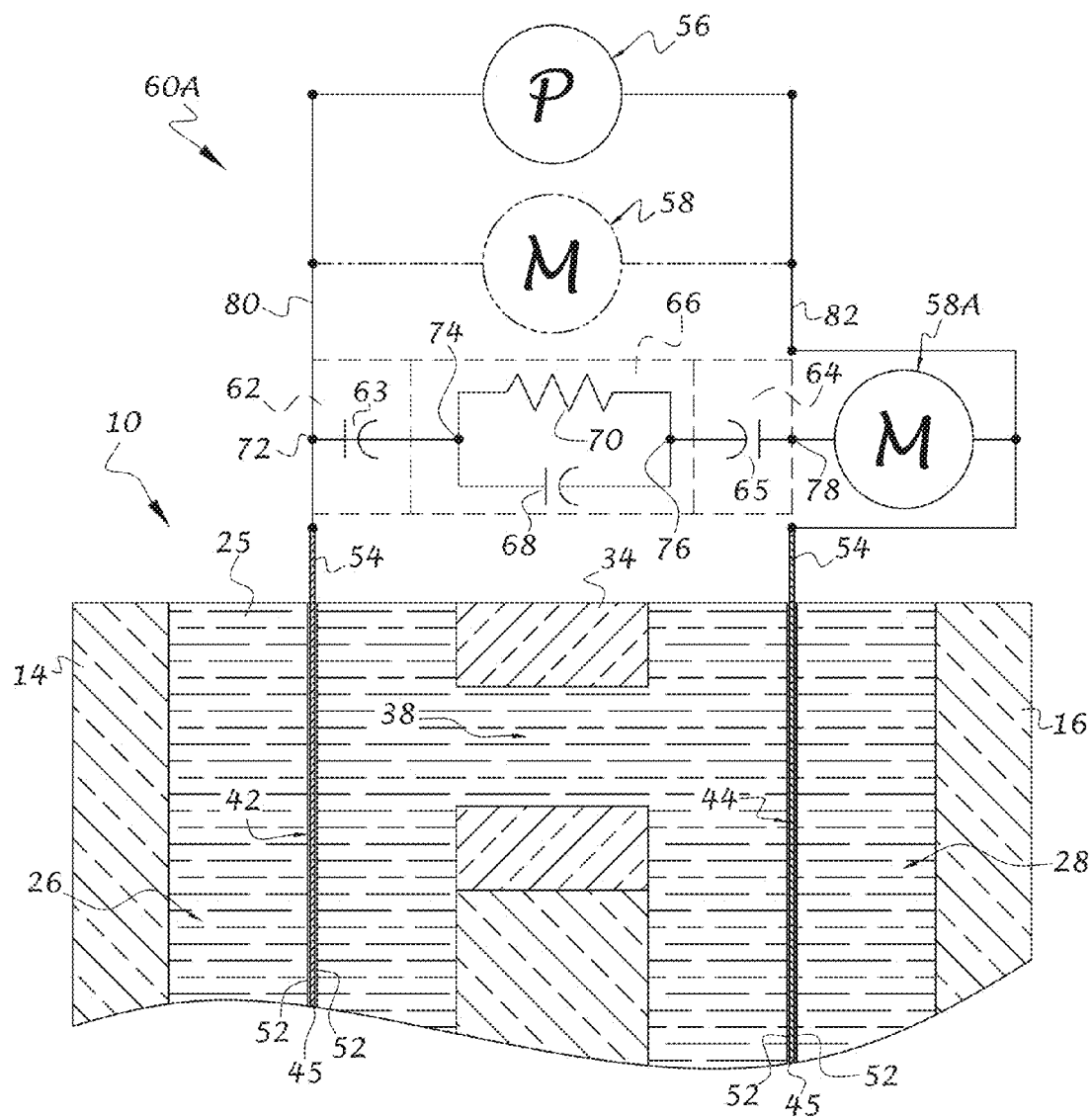
FIG. 7A is a schematic view similar to FIG. 7, with a meter or the like located in series with the equivalent electrical devices for measuring impedance or an electrical current component of the impedance through the system.

Turning now to FIG. 7A, an equivalent electronic circuit 60A is illustrated. The circuit 60A is similar in construction to the circuit 60 as previously described, with the exception that a meter 28A is in series with the equivalent electrical components 62, 66, and 64 of the equivalent electronic circuit in order to measure a change in current during injection of voltage into the system by the power supply 56. The meter 58 can also be present, as shown in phantom line, to also measure impedance of the fluid across one or more of the equivalent electrical components, as previously described.

In general terms, electrical impedance is a measureable property of the equivalent circuit of the fluid under consideration when a voltage is applied across the circuit, and is a measure of the opposition of that circuit to the flow of electrons, i.e. the opposition to the electrical current through the circuit under the applied voltage and/or the residual or resultant electrical current flow through the circuit after the applied voltage has been removed or changed. When direct current is applied to the electrodes 42 and 44 via the power supply 56, impedance and resistance are substantially similar. However, when an alternating current (such as a sinusoidal voltage) is applied to the electrodes 42 and 44, the impedance will have both magnitude and phase components which depend on the properties of the equivalent circuit, and thus in large part on the properties of the fluid, especially with the implementation of one or more reduced flow volumes of the present invention to substantially reduce or eliminate the impedance of the electrodes and insulative layers when in contact with the fluid being measured.

Figure 8:
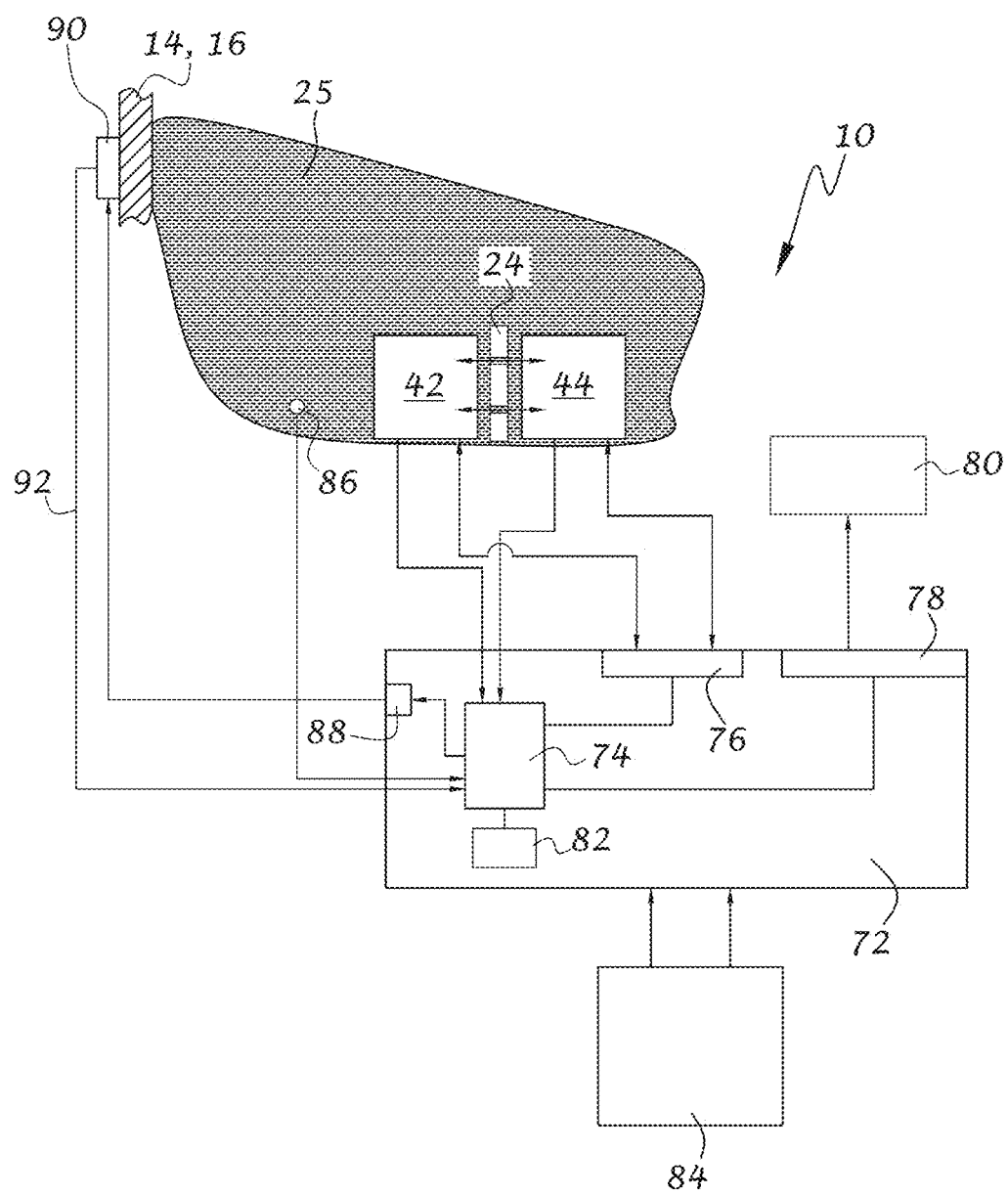
FIG. 8 is a block diagram of an exemplary electronic section of the measurement system of FIG. 1.

As shown in FIG. 8, the measurement system 10 for determining the parameters of a fluid further includes electronic circuitry embodied as an electronics section 70 for generating signals across the electrodes 42 and 44 as well as the fluid 25 between the electrodes, and analyzing resulting signals to determine fluid properties. The electronics section 70 includes a printed circuit board (PCB) 72 with various electronic components mounted thereon or operably associated therewith. The electronic components can include a processor 74, such as a microprocessor or controller for example, a first signal generating module 76 connected to the processor 74 and the electrodes 42, 44 for generating the signals across the electrodes and through the fluid, a signal conditioning module 78 connected to the processor for communicating with a user interface device 80, such as a display, one or more status lights, audible alarms, speakers, radio frequency devices for transmitting signals indicative of the fluid properties to a remote location, and so on. A memory 82 is connected to the processor 74 for storing program instructions, data associated with the fluid, and so on. The electrodes 42 and 44 can be directly connected to the processor 74 to receive and process analog and/or digital signals reflective of the fluid properties being measured or quantified, when the plates and fluid are subjected to a varying voltage generated by the signal generating module 76. The processor can include means, such as software, circuitry, A/D and D/A converters, as well as various electronic components to generate the signals across the electrodes, as well as processing and analyzing the captured data from the electrodes as will be described in greater detail. In this manner, one or more parameters of the fluid being measured based on the captured data from the electrodes can be measured or quantified. Data reflective of the liquid parameter(s) can be stored in the memory device 82 and retrieved for signaling to a user, such as an operator, warranty entity, manufacturer, owner, fleet company, and so on, to indicate whether or not the proper DEF fluid has been put in the reservoir, and thus who may be at fault should a failure occur in the catalytic converter or other system components of the vehicle or equipment due to the use of improper fluid. Such data can also have a time/date stamp associated therewith to pinpoint the moment the improper fluid was introduced and/or used in the system, and thus who may be at fault when failure of one or more system components occurs.

It will be understood that data can be gathered in a similar manner, stored, and retrieved to indicate whether or not other automotive-type fluids (besides DEF) associated with vehicles or machinery, such as fuel, oil, windshield washer fluid, antifreeze, brake fluid, transmission fluid, and so on, are or were inside or outside of specified parameters or quality when first produced and/or introduced into the vehicle, machine, or other system. Thus, capturing data and warning an operator of potential catastrophic damage, as well as recording the introduction of improper fluids for determining who's at fault under warranty and/or repair situations, are made possible by the system 10 of the invention. By way of example, the inadvertent introduction of motor oil into the transmission of an automobile can be catastrophic for the transmission within a very short time period. Thus, the present invention is capable of detecting the introduction of improper fluids within a system with sufficient time to warn an operator before a catastrophic even occurs. It will be further understood that the present invention can be applied to non-automotive fluids, such as processing fluids, fluids in the medical and pharmaceutical industries including intravenous fluids, blood and plasma analysis, body fluid analysis, and so on, fluids in the food industry used for beverages and other consumable products, industrial fluids, and all other fluids that have a measurable change in impedance in accordance with the system and methods of the present invention.

The electronics section 70 can also include a power supply 84 connected to the PCB 72 for powering the various electronic components, a temperature sensor 86 operably connected to the processor for determining the temperature of the fluid 25, since the impedance of the fluid can change with a change in temperature. A second signal generating module 88 can be connected to the processor 74 for generating frequencies in the ultrasonic range to drive a cleaning device 90, which can be connected to a wall 14 or 16 for example, of the measurement housing 12 to clean at least the surfaces of the electrodes 42, 44.

The cleaning device 90 preferably comprises one or more ultrasonic transducers that generate ultrasonic waves between approximately 20 kHz and 400 kHz. When the ultrasonic transducer is driven at higher frequencies, it is capable of cleaning surfaces with more intricate detail than when driven at lower frequencies. The ultrasonic transducer 90 can be constructed of piezoelectric or magnetostrictive materials that can be driven at a predetermined frequency, discrete frequency steps, and/or sweeping frequencies in the ultrasonic bandwidth or at other effective frequencies. In use, one or more transducers is placed at one or more locations on or in the housing 12 and/or other locations where the fluid is subjected to ultrasonic vibration so that particles, contaminants, film, layers, and the like that may tend to collect on, or be in the process of collecting on, the measuring surfaces can be cleaned ultrasonically during fluid flow, when the fluid is stopped, or at any other convenient time for cleaning or ensuring the cleanliness of the measuring surfaces. A feedback loop 92 is also connected between the processor 74 and the transducer 90 for determining when a resonant frequency has occurred so that the transducer 90 can clean the electrodes 42, 44 and other surfaces of the housing 12 in an effective manner.

In order to effectively use the fluid under measurement as the cleaning solution, the driving frequency is shifted to track the resonant frequency shift of the transducer under load by driving the transducer with a sweeping frequency that commences slightly lower than the initial resonant frequency of the transducer to a slightly higher frequency than the resonant frequency of the transducer under load. The resonant frequency may change due to a difference in material properties, ambient temperature fluctuations, differences in fluid properties as the fluid flows through the system, and perhaps for other reasons. Advantageously, no matter what the reason for the resonant frequency shift, this sweeping action automatically picks up the higher frequency of the transducer under load for effective generation of micro cavitation bubbles in the fluid and thus the effective cleaning action of the measuring surfaces, as well as other surfaces that may be in the vicinity and in contact with the fluid. Further details of the system and method for cleaning measurement surfaces are disclosed in U.S. application Ser. No. 14/722,116 filed on May 6, 2015, the disclosure of which is hereby incorporated by reference.

Figure 9:
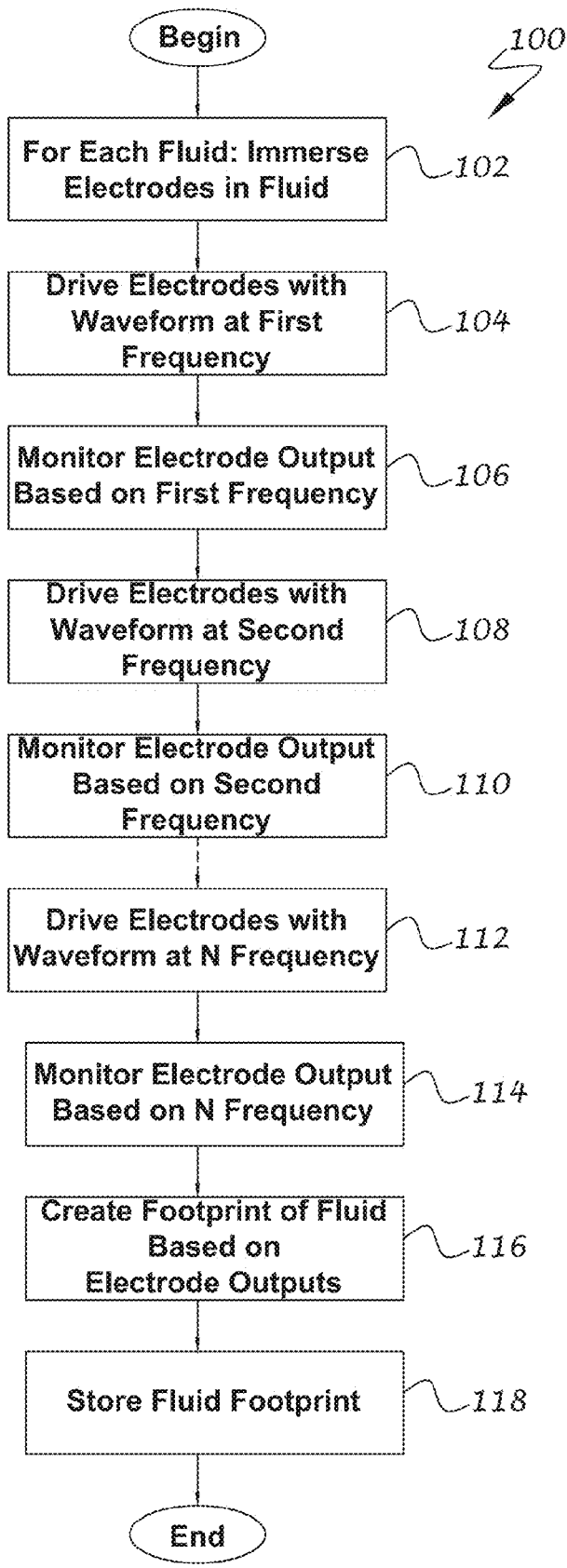
FIG. 9 illustrates an exemplary method in accordance with the invention for determining the quality, fluid composition, and other parameters of an unknown fluid.

Referring now to FIG. 9, a method 100 for determining the footprint of a fluid to be measured is illustrated. The ultimate purpose of the method 100 is to measure known fluids and known fluid mixtures or combinations of fluids, as well as undissolved components that may be located in the fluid, in various percentages that can be quantified separately and independently, in order to determine different footprints of known fluids. Unknown fluids are then measured the same way, a unique footprint is determined for the unknown fluid, and the unique footprint is compared against the predetermined footprints of known fluids, to thereby identify the unknown fluid with a relatively high degree of confidence. The method of identifying an unknown fluid will be described in greater detail below with respect to FIG. 16.

The method 100 includes filling the housing 12 with fluid so that the electrodes 42, 44 are completely immersed in the fluid, or at a predetermined level on the electrodes for each fluid, as shown at block 102. It will be understood that the electrodes can alternatively be immersed by dipping the electrodes into the fluid and/or filling the housing 12 with fluid to a predetermined level. At block 104, a waveform voltage at a first frequency is then driven across the electrodes, the insulation surrounding the electrodes, and the fluid being measured. The electrode output based on the first frequency is monitored at block 106. The electrical output is preferably monitored and recorded as a change in electrical current, such as the flow or resistance to flow, of electrons through the system, but can additionally or alternatively comprise monitoring any component of the fluid impedance under an applied electric field, as previously described with respect to FIGS. 7 and 7A, including changes in voltage, capacitance, resistance, inductance, frequency response, etc., without departing from the spirit and scope of the invention. The monitored output can greatly vary depending on the properties of the liquid, the thickness of the insulative layer, the surface areas of the electrodes, the space between the electrodes, as well as the size of one or more reduced flow volumes located within the liquid between the electrodes. At block 108, a waveform voltage at a second frequency is then driven across the electrodes, the insulation surrounding the electrodes, and the fluid being measured. The electrode output based on the second frequency is monitored and recorded at block 110. Again, the measured output is preferably arranged to monitor and record a change in the current flowing through the system, or an opposition to current flow. However, it will be understood that other properties of the circuit can be monitored as described above with respect to the first wave form. The property being measured is not as important as the consistency in measurement of that property during application of the different frequencies across the fluid under consideration. At block 112, the above-described process can be repeated until a predetermined number of times, represented by the value "n", has been reached, with each time representing a different frequency applied to the circuitry. The output of each frequency is monitored and recorded, as shown at block 114. The outputs of all frequencies, a range of frequencies, or selected frequencies, are then combined to form a signature or footprint of the particular fluid that has just been measured, as shown at block 116. The footprint for the fluid is then stored in a memory location associated with the processor for retrieval, as shown at block 118. The above-described process is repeated for several "known" fluids or known combinations of fluids, in order to obtain standardized signatures or footprints for each fluid or combinations of fluids. These footprints can then be accessed when measuring an unknown fluid to thereby identify that fluid, as will be described in greater detail below.

Figure 11:
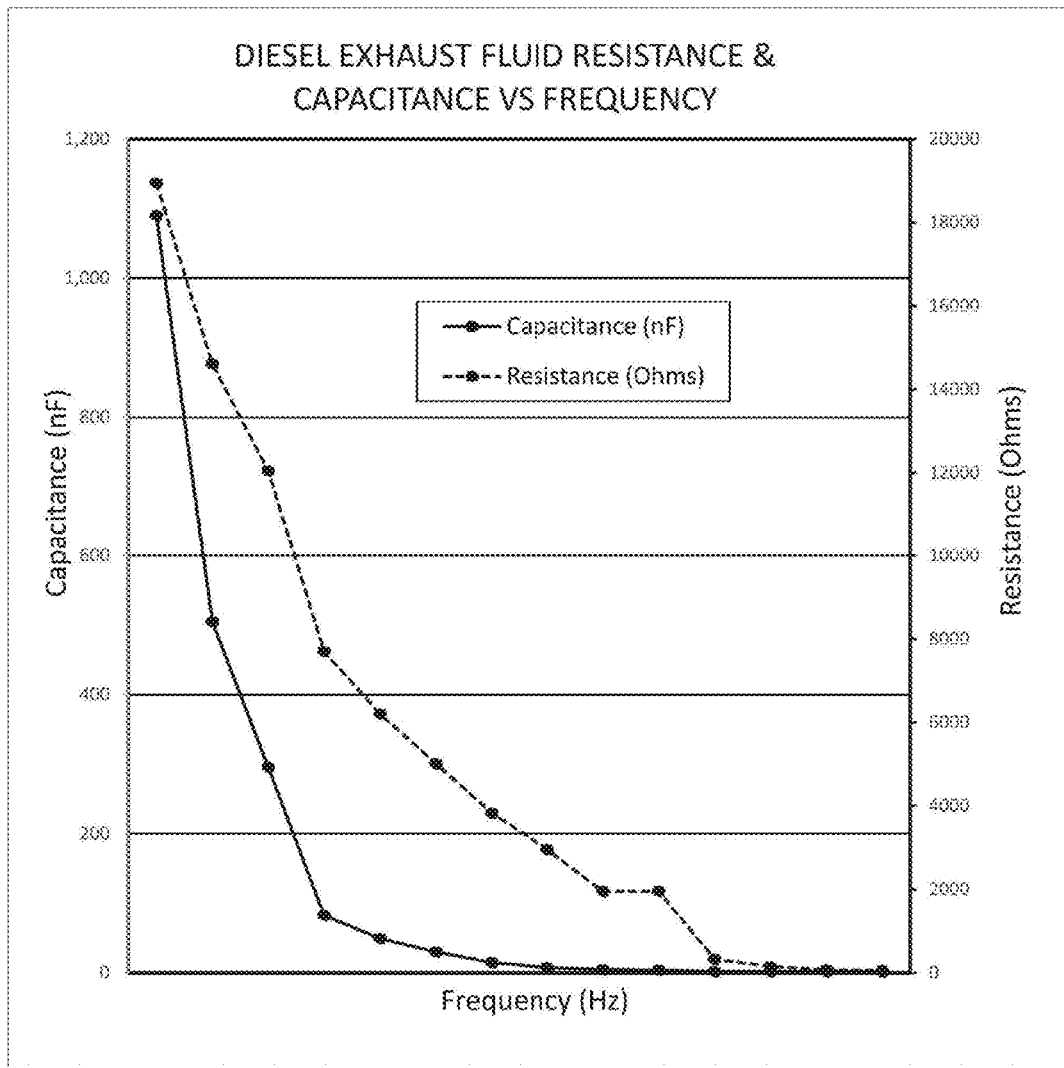
FIG. 11 shows a logarithmic graph of the chart data in FIG. 10.

Referring now to FIGS. 10 and 11, a chart and graph are illustrated, respectively, showing raw data of diesel exhaust fluid (DEF) gathered using the above-described exemplary fluid measurement system 10 (FIG. 1). Frequencies of 20, 50, 100, 500, 1 k, 2 k, 5, 10 k, 20 k, 50 k, 100 k, 200 k, 500 k, and 1 MHz were applied across the electrodes 42, 44, insulative layers, DEF, and reduced flow volumes or spaces 38 between the electrodes 42 and 44. Each frequency setting yielded a different value for resistance and capacitance. The capacitance values, measured in Nano-Farads, were relatively high at lower frequencies and relatively low at higher frequencies. The resistance values, measured in Ohms, were also relatively high at lower frequencies and relatively low at higher frequencies. This phenomena is unique to the particular fluid being measured and can greatly vary depending on the fluid properties, including composition, density, conductivity, temperature, and so on. Accordingly, a unique signature or footprint can be obtained for different fluids using the above-described method 100 (FIG. 9). It will be understood that the particular frequencies, the fluid measurement system 10, as well as the resultant impedance, such as the resistance and capacitance values of the DEF, are given by way of example only, as different frequencies, ranges of frequencies, the number of frequencies, as well as the resultant components of the impedance of the fluid(s) being measured, can greatly vary without departing from the spirit and scope of the invention.

Referring now to FIGS. 12-15, several graphs were obtained using the above-described exemplary fluid measurement system 10 (FIG. 1) and the above-described method 100 (FIG. 9). Each graph represents a derived fluid signature or footprint with frequencies ranging from 20 Hz to 1 MHz and the resultant resistance (in Ohms) at each frequency. It will be understood that instead of or in addition to resistance measurements, any and/or all of the components of the resultant fluid impedance can be plotted. Accordingly, each fluid signature or footprint can be a single component or a plurality of components of the impedance as discussed above, including for example, voltage, current, inductance, resistance, capacitance, and/or resultant frequency, etc., of the fluid, versus the applied frequency. Depending on the fluid type, it may be advantageous to select one or more components of the impedance over others as the selected components may be more prevalent or give greater bandwidth or resolution.

Figure 12:
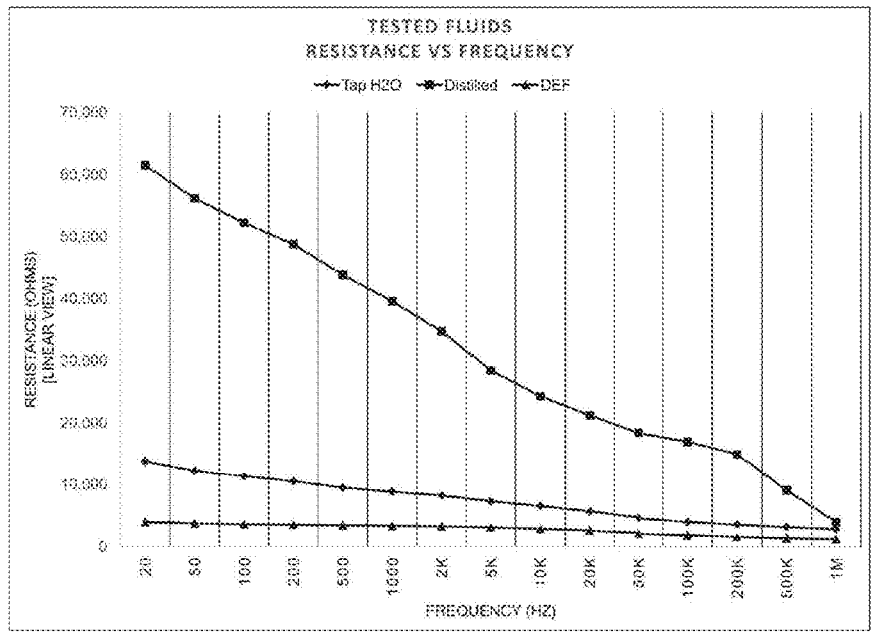
FIG. 12 illustrates a third chart of raw data gathered representing a first electrical characteristic in accordance with the first exemplary data gathering method of the invention representing fluid signatures for tap water, distilled water, and commercial diesel exhaust fluid (DEF) with 32.5% urea in deionized water is illustrated.
Figure 13:
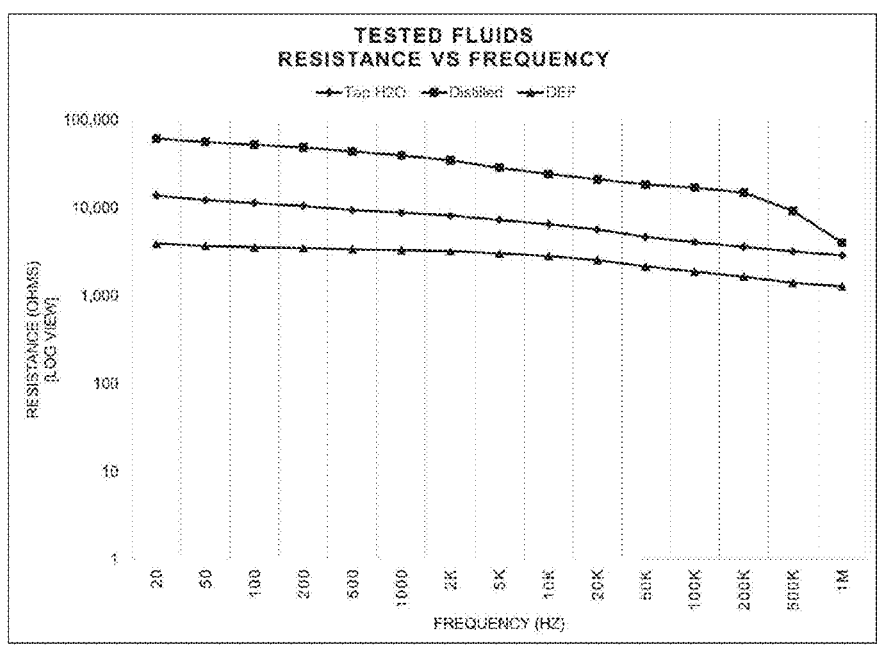
FIG. 13 is a chart similar to FIG. 12 with the data represented in logarithmic form.

With particular reference to FIGS. 12 and 13, fluid signatures for tap water, distilled water, and commercial diesel exhaust fluid (DEF) with 32.5% urea in deionized water are illustrated. The DEF is commercial grade and intended for SCR systems to reduce or eliminate contaminants in the exhaust of diesel powered vehicles or equipment. The use of any other fluid in such systems besides commercial grade DEF can be detrimental to the components of the exhaust system, such as the catalytic converter, as well as the environment. As shown, each fluid has a unique signature and is therefore readily identifiable when an unknown fluid having the same characteristics is measured. In FIG. 13, a logarithmic scale of the same fluids is plotted, with differences between the fluids being an approximate order of magnitude of 5 between the DEF and tap water, and an approximate order of magnitude of 10 between the tap water and distilled water. Accordingly, the high measurement bandwidth of the present invention results in a high statistical probability that an unknown fluid can be successfully identified.

Figure 14:
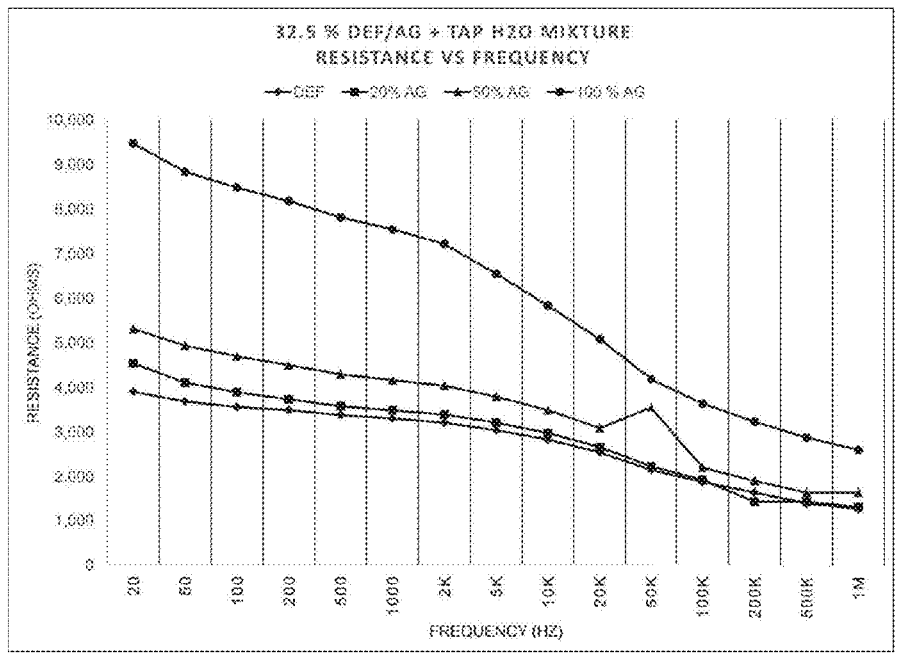
FIG. 14 shows a fifth chart with signature data of various percentages of agricultural grade (AG) urea in tap water (32.5% AG urea) compared with DEF (32.5% high grade urea in deionized water) as measured in accordance with the first exemplary data gathering method of the invention, where the AG DEF is misleading at the ideal 32.5% urea concentration as measured with a prior art DEF quality sensor.

As shown in FIG. 14, the raw signature data of various percentages of agricultural grade (AG) urea in tap water (32.5% AG urea) with DEF (32.5% high grade urea in deionized water) are illustrated. As in the previous charts, each graph represents a derived fluid signature or footprint with frequencies ranging from 20 Hz to 1 MHz and the resultant resistance (in Ohms) at each frequency. As shown, commercial grade DEF is the lowest footprint on the chart, followed by the footprint of 20% AG grade DEF with 80% commercial grade DEF, then the footprint with 50% of each fluid, and finally 100% AG grade DEF. The great disparity between 100% AG grade DEF and the other fluids is most likely due to the higher conductivity (the lower purity) of the AG grade DEF. Accordingly, it is possible with the system and method of the invention to distinguish between different mixtures of acceptable and unacceptable DEF fluids, as may be experienced in real scenarios, especially in the agricultural industry where low-grade low-cost urea is readily available. In prior art devices, it has not been possible to distinguish between the higher and lower grades of urea, let alone mixtures thereof. The presence of low-grade AG DEF, as may be mixed up by the consumer, does not offer the same benefits as the commercial grade DEF, and thus may damage the associated system and/or be ineffective at reducing diesel exhaust emissions.

Figure 15:
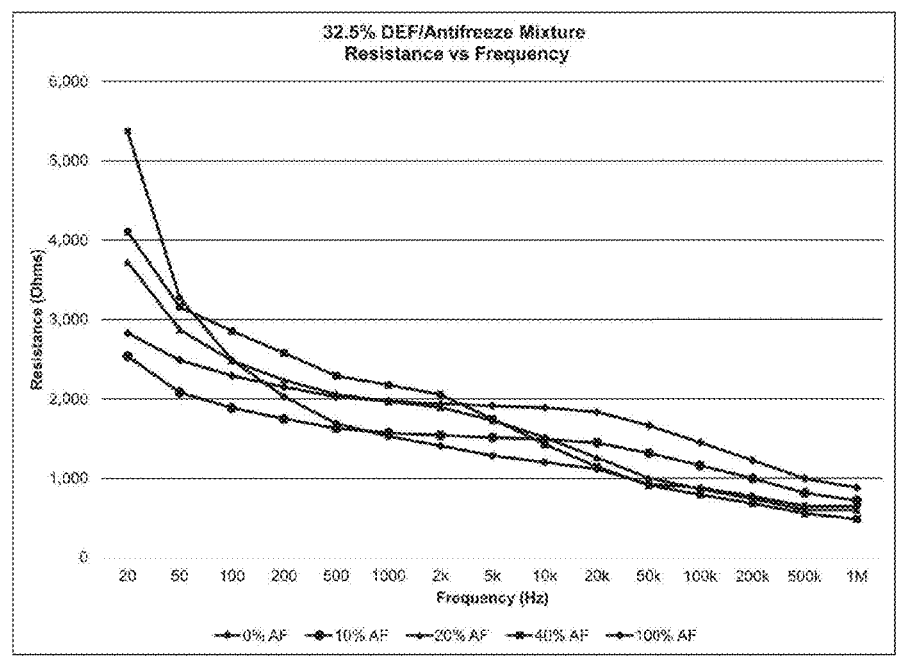
FIG. 15 is a sixth chart showing the raw signature data of various percentages of 50% antifreeze mixture with DEF (32.5% high grade urea in deionized water).

With reference to FIG. 15, the raw signature data of various percentages of 50% antifreeze mixture with DEF (32.5% high grade urea in deionized water) are illustrated. As in the previous charts, each graph represents a derived fluid signature or footprint with frequencies ranging from 20 Hz to 1 MHz and the resultant resistance (in Ohms) at each frequency. Visible differences in signatures can be seen between DEF without antifreeze, DEF with 10%, 20% and 40% antifreeze mixtures, and the antifreeze mixture without DEF. The presence of antifreeze in the system is a real world possibility since DEF tanks typically include heating tubes with antifreeze flowing therethrough in order to thaw and warm the DEF in low temperatures. In the event of a leak or break in the heating tubes, the detection of even small portions of antifreeze is advantageous so that the system and/or operator can be alerted to the contaminated DEF and take positive action to resolve the problem. An operator may also inadvertently put antifreeze or other fluids in the DEF tank, which could cause damage to the system and/or defeat its purpose to reduce emissions. Accordingly, the present invention is advantageous in detecting and identifying different fluids and fluid mixtures in automotive as well as other applications, as previously described.

Figure 16:
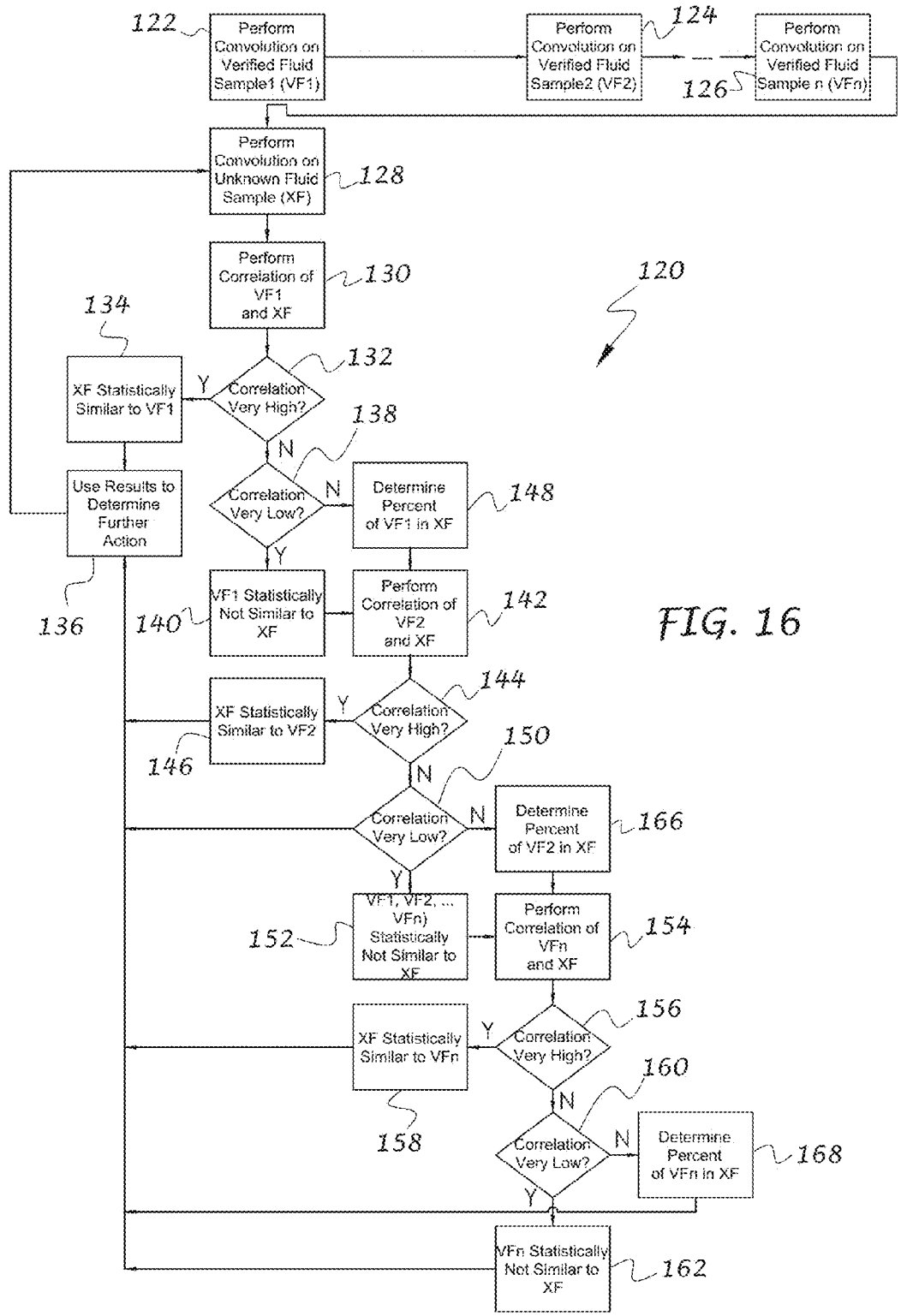
FIG. 16 illustrates an exemplary method according to the invention for obtaining unique identification signatures for known fluids and determining an unknown fluid by comparing the measured signature of the unknown fluid with the signatures of the known fluids.

Turning now to FIG. 16, a method 120 of determining the properties of an unknown fluid is illustrated. At blocks 122, 124, and 126, a number of signatures or footprints are established for verified fluid samples as described above, wherein a plurality of frequencies for each fluid have been applied to the fluid, monitored, and stored in memory, then compared with an unknown fluid under consideration, in what can be termed a frequency analysis, or in accordance with a further embodiment of the invention what can be termed a convolution, to define the particular signature or footprint for the unknown fluid. For example, frequency analysis or convolutions are performed for obtaining footprints for a Verified Fluid Sample 1 (VF1) at block 122, a Verified Fluid Sample 2 (VF2) at block 124, and so on, until a Verified Fluid Sample n (VFn) at block 126 has been obtained, where "n" represents the final sample in the series of samples, which can comprise a single sample to more than thousands of samples. The number of known fluid samples, as represented by stored data in one or more databases for example, can greatly vary, and may be largely dependent on whether the present invention is embodied as a general purpose fluid identification device or as a specialized fluid identification device for identifying a more specific set of unknown fluids or variations of a particular fluid.

Once the desired number of footprints have been obtained for the preselected known fluids, a frequency analysis or convolution is performed on an unknown fluid sample (XF) at block 128. This can include filling the housing 12 (FIG. 1) with the unknown fluid sample (XF) in a consistent manner with the previously measured known fluid samples, then applying the same waveform voltages at the same frequencies and in the same sequence across the electrodes, the insulation surrounding the electrodes, the fluid being measured, and the restricted flow volumes. The electrical output is monitored in the same way as the known fluid samples and data is collected and stored to obtain the signature or footprint of the unknown fluid sample (XF).

At block 130, a correlation is performed between known fluid sample VF1, for example, and the unknown fluid sample XF. It will be understood that performing the correlation can begin with a data set representative of the signature of any known fluid sample and therefore does not necessarily need to start with a particular known fluid data set or follow a predetermined order when correlating with other know fluid samples. At block 132, it is determined whether or not the the signature data of XF has a very high correlation with VF1 (or other known fluid). If yes, it is determined at block 134 that XF is statistically similar to VF1, i.e. there is a very high probability that the unknown fluid has been identified as the known fluid VF1. The correlation can be performed by comparing data points of the two fluids at each frequency and determining if the values of the corresponding data points of both fluids at the particular frequencies are closely similar or equal. The correlation can also be performed by comparing the overall footprint of VF1 with the overall footprint of XF through statistical analysis. It will be understood that other methods for determining the correlation, or the lack of correlation, between the footprints of the known fluids and fluids under test can be used without departing from the spirit and scope of the invention.

At block 136, the results of that determination are used to take further action, such as recording the analysis in memory for retrieval, alerting an operator that a correct fluid or incorrect fluid is present in the machine, system, or device, taking automatic control of the system in the event the fluid has been identified as the incorrect fluid for the system, allowing operation of the system in the event the fluid has been identified as the correct fluid for the system, changing a flow rate of the fluid entering the system, automatically mixing the determined fluid with one or more known fluids to obtain a predetermined ideal mixture or solution for the system, and so on.

By way of example, if the system is a SCR system that requires diesel exhaust fluid with a mixture of 32.5 percent urea in deionized water, and further if the known fluid VF1 is windshield washer fluid, and the fluid XF is also identified as windshield washer fluid, the system can be shut down, the operator can be alerted that incorrect fluid has been entered into the system, the time and date of the incorrect fluid determination can be recorded or registered for liability or warranty purposes, and so on. If however, in the present example, the known fluid VF1 is the proper ratio of DEF fluid and the fluid XF is also identified as the proper ratio, then the SCR system remains operational. In any event, the fluid in the system can continue to be monitored at block 128 as described above.

If at block 132 it has been determined that a very high correlation does not exist between VF1 and XF, it is determined at block 138 whether or not the correlation is very low. If the correlation between VF1 and XF is very low, it is determined at block 140 that VF1 and XF are not statistically similar. The unknown fluid sample XF is then compared to the next known fluid sample VF2 at block 142. At block 144, it is determined whether or not the signature data of the unknown fluid sample XF has a very high correlation with the signature data of the second fluid sample VF2 (or other data associated with another known fluid). If a high correlation is present between the two fluids, it is determined at block 146 that XF is statistically similar to VF2, i.e. there is a very high probability that the unknown fluid XF has been identified as the known fluid VF2. Further action is then initiated at block 136, as previously described with respect to the correlation of XF with VF1, for example.

If however at block 144 it has been determined that a very high correlation does not exist between VF2 and XF, it is determined at block 150 whether or not the correlation is very low. If the correlation between VF2 and XF is very low, it is determined at block 152 that VF2 and XF are not statistically similar. The unknown fluid sample XF is then compared to the next known fluid sample, such as a third known fluid sample VF3 (not shown), and so on, until the nth known fluid sample VFn, as indicated at block 154. If it is determined at block 156 that a high correlation exists between the data of the unknown fluid XF and the data of the nth known fluid VFn, it is determined at block 158 that XF is statistically similar to VFn, i.e. there is a very high probability that the unknown fluid XF has been identified as the known fluid VFn. Further action is then initiated at block 136, as previously described, for example. If however at block 156 it has been determined that a very high correlation does not exist between VFn and XF, it is determined at block 160 whether or not the correlation is very low. If the correlation between VFn and XF is very low, it is determined at block 162 that VFn and XF are not statistically similar.

The unknown fluid sample XF is therefore determined as unidentifiable with the available data sets relating to the known fluids, and further action can be taken at block 136 as previously described so that the system associated with the fluid, the operator, and so on, can be alerted that an unknown fluid is present. Since the presence of unknown fluid is normally not a desirable condition of the system, further action can be taken to protect the system from damage or failure that may result because of the unknown fluid.

Referring again to block 132, if it has been determined that the correlation between the unknown fluid XF and the known fluid VF1 is not very high, then at block 138 it has been determined that the correlation between the fluids is not very low, it is then concluded that there are some statistical similarities between the known fluid VF1 and the unknown fluid XF. AT block 148, the degree of statistical similarity can then be used to determine a percent of the known fluid VF1 located in the unknown fluid XF, which for purposes of description only will be labeled VF1-XF. In order to further identify the contents of the unknown portion of the fluid VF1-XF, a further correlation is performed between the fluid VF1-XF with the known fluid VF2 (or other known fluid data). Since in this case there will not be a very high correlation between VF1-XF and VF2, as determined at block 144, then at block 150 it is determined if the correlation between these fluids is very low. If the correlation is very low, then at block 152 it is determined that VF2 is statistically not included in the VF1-XF fluid, and a further correlation is performed between VF1-XF and another known fluid, such as VFn, as shown at block 154.

If however the correlation is not very low between VF1-XF and VF2, then at block 166 that fluid VF2 is indeed statistically part of the fluid VF1-XF. This process can continue with further correlations with further known fluids, as represented at blocks 156 and 160. Finally, at block 168, if the correlation between VF1-XF and VFn is neither high nor low, then it is determined that a percent of VFn is also included in the VF1-XF fluid. The particular amount or percentage of VFn in VF1-XF is dependent on the particular level of correlation between the fluids. Once the unknown fluid has been completely identified or even partially identified, the results are used to determine further action at block 126, as previously described. The process is then repeated at block 128 where the fluid in the system is assumed as unknown, even when the unknown fluid has been identified, since the system normally will not have control over changes in fluid properties, such as degradation or the addition and/or replacement of the correct fluid with one or more incorrect fluids.

Figure 17:
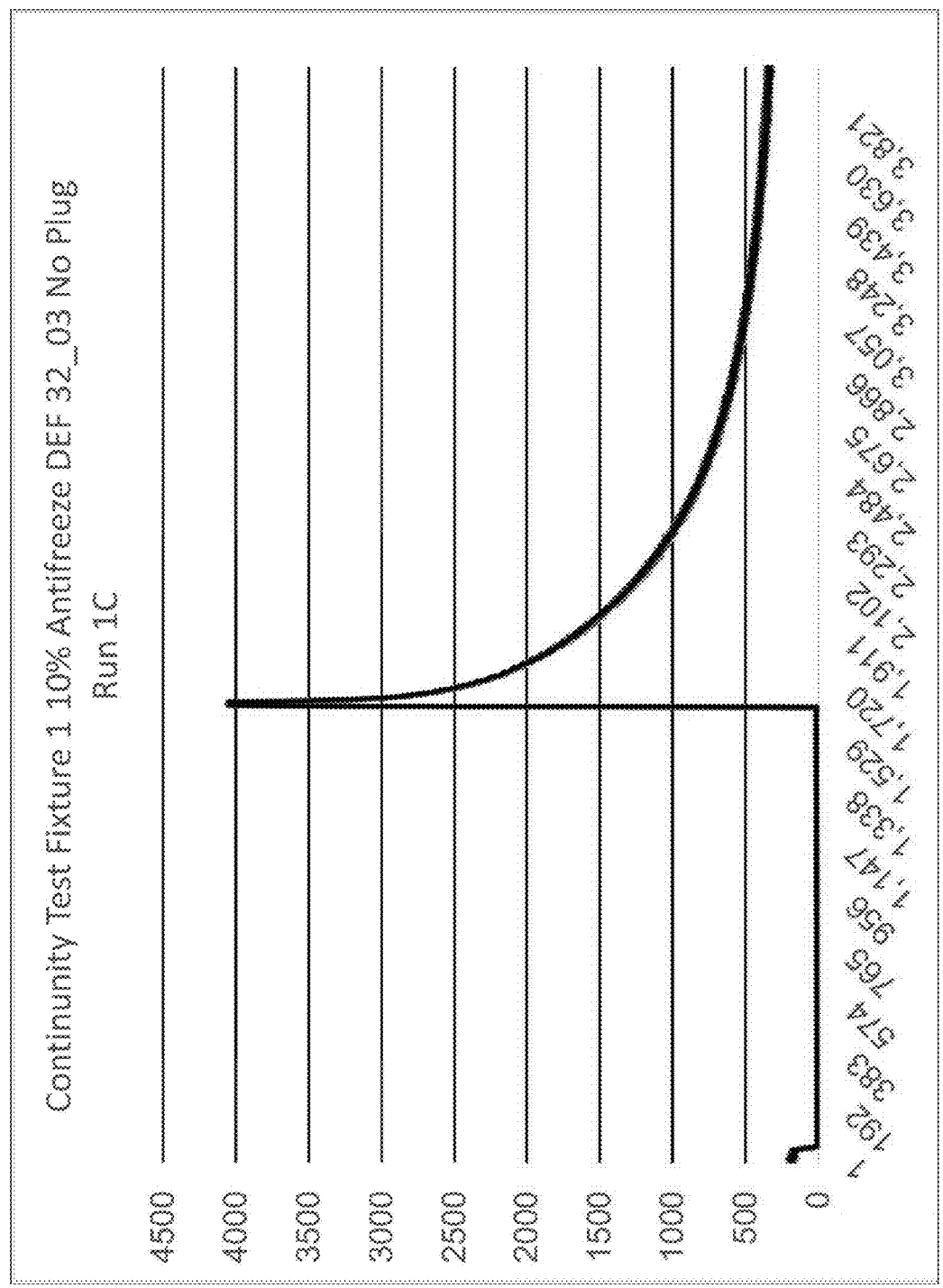
FIG. 17 is a first chart of raw data gathered in accordance with the second exemplary data gathering method of the invention showing a particular fluid signature.

Referring now to FIG. 17, a graph 130 is illustrative of the properties of a fluid obtained from a method for determining the footprint of a fluid to be measured in accordance with a further embodiment of the invention. In the previous embodiment, a finite number of frequencies were applied, by way of example, to various fluids being measured to obtain a unique footprint for each fluid and to identify an unknown fluid once the footprints for known fluids had been established. The particular number of frequencies, which in the previous embodiment were applied sequentially while measuring the frequency response of the fluid as discussed above, is largely dependent on the computing power of the processor, the amount of available memory for storing data, as well as other related factors. Where it is desirous to implement a cost-effective system that can be widely used in traditionally cost-competitive industries, such as the automotive industry, the method of the present embodiment of the invention is capable of decreasing the computing power, processing time, and memory space required to collect data, while greatly increasing the number of frequencies that can be applied to the fluid being measured.

Accordingly, in accordance with the present embodiment, a digital signal processing technique includes applying a voltage pulse to the measurement system, including the electrodes, insulation, fluid being measured, and one or more impedance modifiers if present. The voltage pulse is preferably a square wave pulse that comprises an infinite summation of sinusoidal waves and their harmonics. The output of the square wave pulse can be analyzed, using its properties such as pulse height, pulse width, rise time, fall time using current or calculated voltage information, for example, to define the frequency and magnitude of all of the sine waves at different frequencies that comprise that pulse. This can be done through what can be termed a convolution, by the use of a Fourier Transform (FT) mathematical algorithm or the like. Although this algorithm may be too complex for many microprocessors where cost is a sensitive factor, a convolution method utilizing Fast Fourier Transform (FFT) can be used, which provides essentially the same output with much less processing power requirements. The FFT method is thus more readily adaptable to low-cost microprocessors, and is a preferred technique used in the present embodiment.

When an electrical pulse is applied to the input of the above-described system 10 for example, the output can be defined as the summation of all sine wave frequencies and their harmonics to form a unique signature for the fluid being measured. With the method of the previous embodiment, a finite number of frequencies were input into the system, resulting in a finite number of data points associated with those frequencies. In the above example, approximately 15 different frequencies were used to define the signature of the fluid. In the present embodiment of the invention, the application of a square-wave pulse essentially permits virtually an infinite number of frequencies between predetermined upper and lower frequency limits to be simultaneously applied to the system, resulting in a very large number of data points to thereby more accurately define the fluid signature or footprint at a much higher resolution.

In FIG. 17, the fluid being measured was DEF with 32.0 percent urea in deionized water, with a 10 percent mixture of 50% antifreeze. The Y-axis is divided in "bits" as the data being collected passed through a 12-bit A/D converter before being processed by the microprocessor, and therefore 4,096 bits are available, which represents the current output of the system. The particular value of the current is not as important as the change in value over time. The X-axis is labeled with the number of data samples or readings taken at discrete intervals of time, such as every 10 micro-seconds for example. The X-axis is labeled from 0 to 3,934 samples taken at the discrete intervals, and thus represents a particular time period for all samples gathered. The particular time a sample is taken, or the particular time between samples, are not as important as the change in current relative to the last sample or reading taken. It will be understood that the particular values can greatly vary, the invention is not limited to a particular A/D converter, and the graph can be configured in any convenient manner as long as a particular footprint can be obtained that is unique to a particular fluid being measured, without departing from the spirit and scope of the invention.

At approximately sample No. 70, noise in the system has begun to stabilize out and the electrical current is at or near zero. At approximately sample No. 1,657, or at time=0, a sudden transition voltage is applied across the system, including the electrodes, insulation layers, and the fluid being measured, as well as the reduced flow volumes or spaces. The voltage pulse in this example is a square wave pulse comprising a virtually infinite number of sinusoidal frequencies summed together. At this point, the current spike is above the capacity of the 12-bit A/D converter used to convert the analog current samples to digital data before being processed by the microprocessor. The magnitude or peak of the current spike is indicative of the resistance value of the fluid, while the decay time is indicative of the capacitance value of the fluid. The degradation curve following the spike, between sample Nos. 1,657 and 3,934, is a function of both the capacitance and resistance of the fluid, as well as other impedance characteristics of the fluid, such as inductance. The particular resistance, capacitance, inductance, and other electrical impedance characteristics of the fluid are not as important as the actual degradation curve itself and the shape of the curve. The resultant degradation curve over a decay time period is characteristic of the summation of the sinusoidal frequencies in response to the properties of the fluid, and is largely dependent on the conductance or impedance of the fluid being measured. The current decay rate through the fluid is monitored via a FFT analysis for each frequency in the electrical current waveform to obtain the signature or footprint of the fluid being measured, as shown in FIG. 17.

Figure 18:
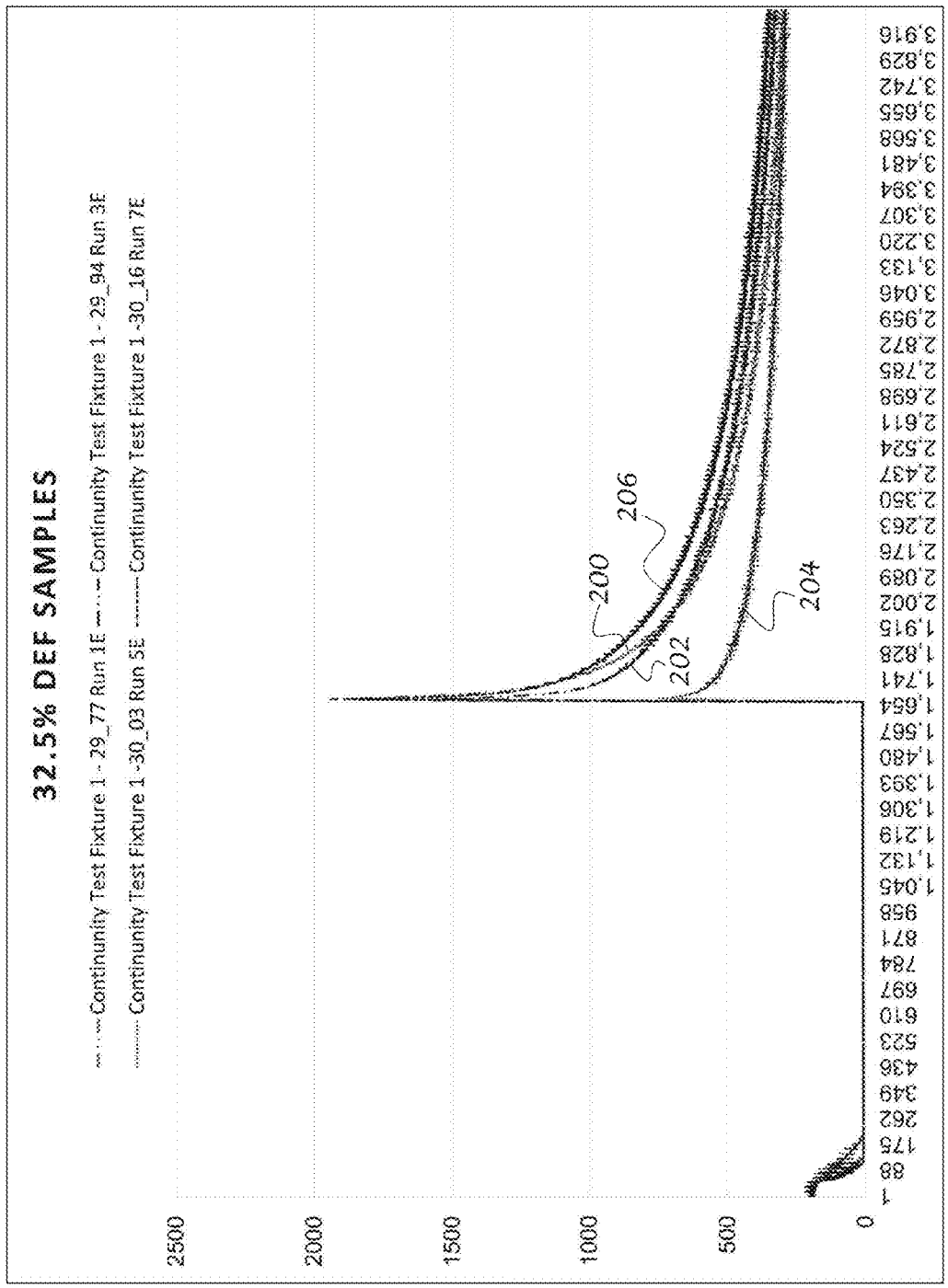
FIG. 18 is a second chart of raw data showing different unique fluid signatures for DEF having slightly different concentrations of urea.

Referring now to FIG. 18, a chart illustrating the footprints of various DEF samples generated by applying an electronic pulse to the system in accordance with the present invention is shown. Fluid samples include DEF with 29.77, 29.94, 30.03, and 30.16 urea percentages in deionized water corresponding with footprints 200, 202, 204, and 206, respectively. As shown, an electronic pulse was applied to the fluids, with each fluid having a different current peak indicative of fluid resistance. Each fluid also has a different electrical current decay profile, indicative of fluid capacitance. The present invention is therefore capable of distinguishing between small differences in the amount of urea in the DEF. The present invention is also capable of distinguishing between small differences in other fluids, and therefore is not limited to the measurement and determination of fluids with urea content.

Figure 18A:
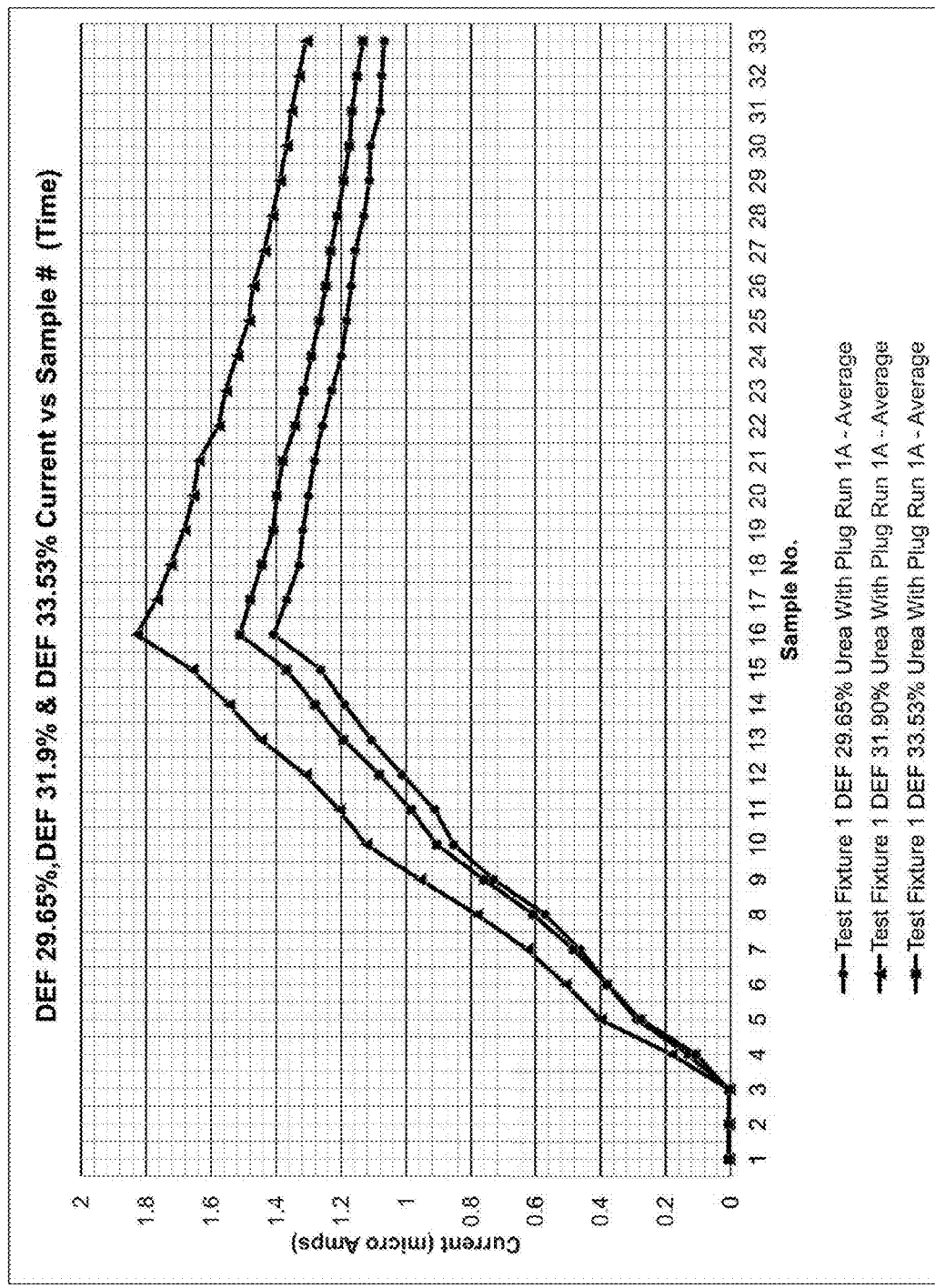
FIG. 18A is a third chart of raw data showing an expanded portion of different unique fluid signatures for commercial grade DEF having different concentrations of urea ranging from 29.65% to 33.53% urea in deionized water.
Figure 19:
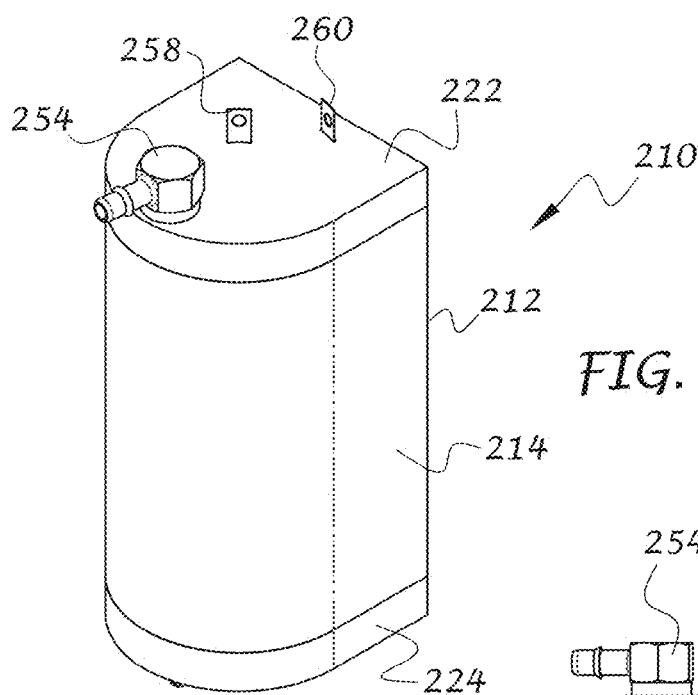
FIG. 19 is an isometric view of a measurement system for determining fluid quality and other parameters in accordance with a further exemplary embodiment of the present invention.
Figure 20:
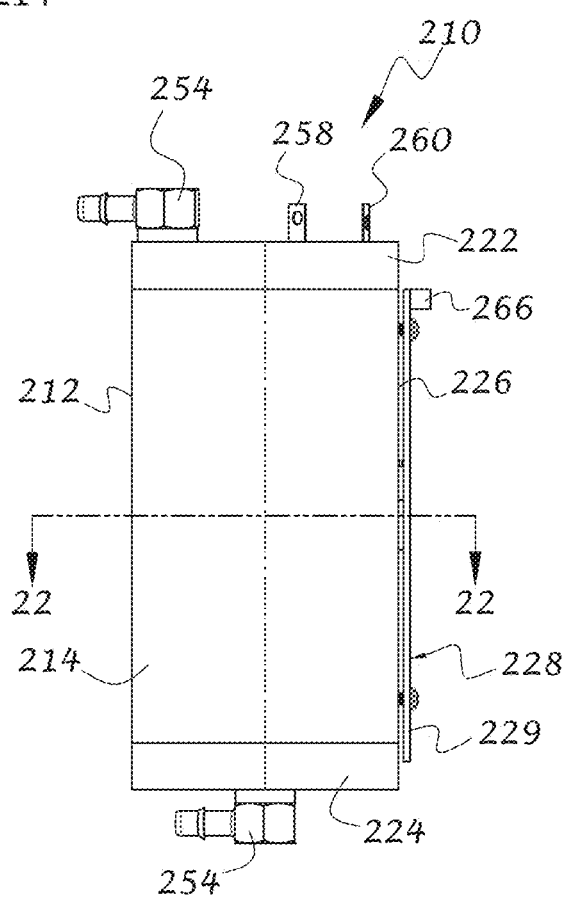
FIG. 20 is a left side elevational view thereof.
Figure 21:
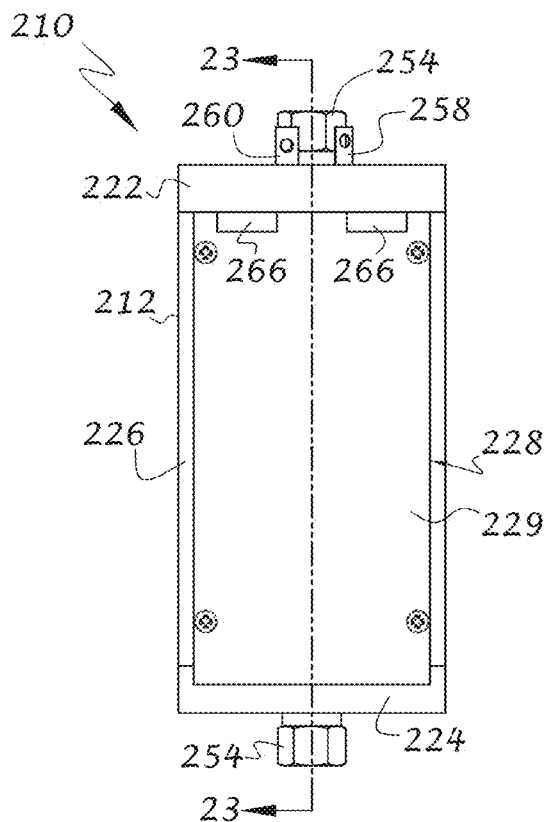
FIG. 21 is a rear side elevational view thereof.
Figure 22:
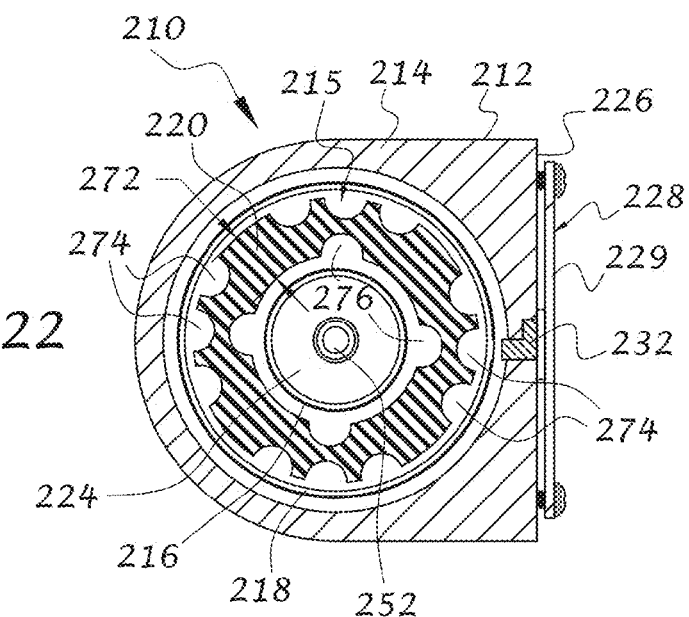
FIG. 22 is a sectional view thereof taken along line 22-22 of FIG. 20.
Figure 23:
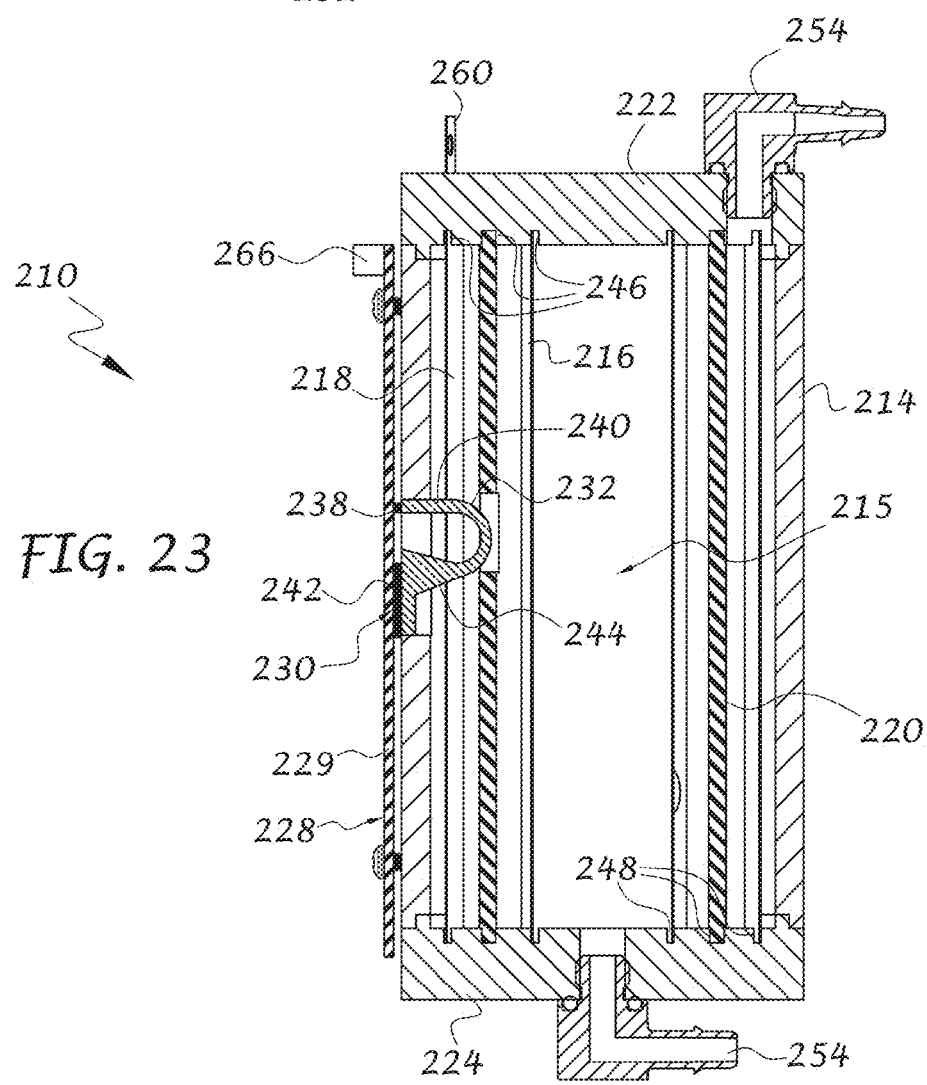
FIG. 23 is a longitudinal sectional view thereof taken along line 23-23 of FIG. 21.

Referring now to FIG. 18A, a chart illustrating the footprints of various DEF samples generated by applying an electronic pulse to the system in accordance with the present invention is shown. Fluid samples include DEF with 29.65, 31.90, and 33.53 percent of urea in deionized water. As shown, an electronic pulse was applied to all of the fluids, with a slope of the electrical pulse indicative of the expanded range of the chart when compared to previous charts, as denoted by the relatively small amount of sample numbers (reflective of time since each sample was taken at a predetermined time interval) along the X-axis. As shown, each fluid has a different current peak indicative of fluid resistance. Each fluid also has a decay profile, indicative of fluid capacitance. Each fluid also has a slightly different rise time as the initial pulse is being applied, which is a further indicator of the difference in impedance of the fluids. The present invention is therefore capable of distinguishing between larger differences in the amount of urea in the DEF. The present invention is also capable of distinguishing between larger differences of various constituents in other fluids, and therefore is not limited to the measurement and determination of fluids with urea content.

Referring now to FIGS. 19-24, a system 210 for determining fluid composition and/or fluid quality is illustrated. The system 210 preferably includes a housing 212 having a continuous side wall 214 that defines a cylindrically-shaped interior or reservoir 215 (FIGS. 22 and 23) for holding a quantity of fluid to be measured. The reservoir 215 receives a first or inner annular electrode 216 and a second or outer annular electrode 218 coaxial with the first electrode. An electrically insulative annular impedance modifier 220 is also positioned coaxially in the reservoir 215 between the inner and outer electrodes 216, 218 respectively. The impedance modifier 220 surrounds the inner electrode 216 and is surrounded by the outer electrode 218 to restrict the flow of electrical current between the electrodes, as previously described with respect to the FIG. 1 embodiment. A top cap 222 and a bottom cap 224 are located at opposite sides of the housing 212 to enclose and seal the hollow interior 214 and its contents, including the fluid passing therethrough.

Figure 24:
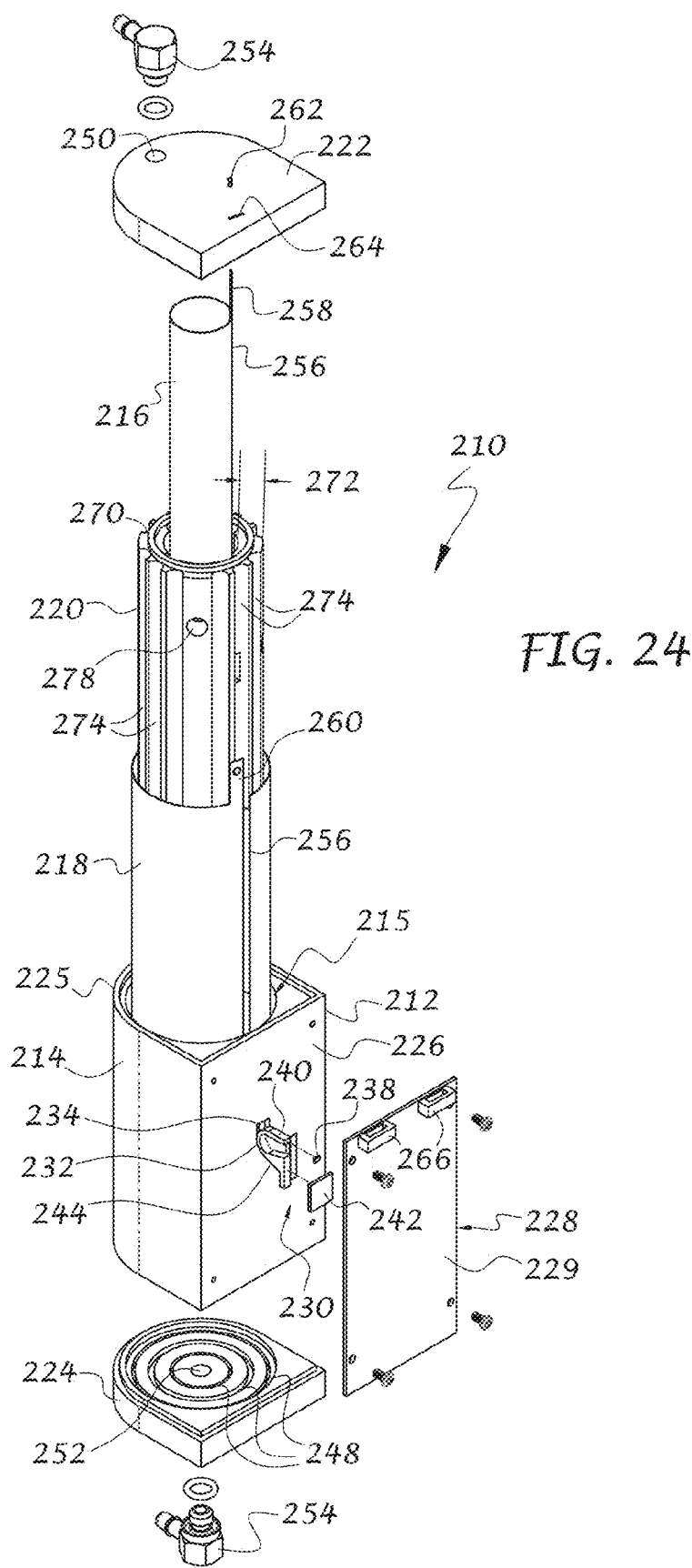
FIG. 24 is an exploded isometric view thereof showing similar principles of operation as the previous exemplary measurement system of the invention.

As best shown in FIG. 24, the continuous side wall 214 of the housing 212 has a first side wall section 225 that is semi-circular in cross-section and a second flat wall section 226 that receives an electronic assembly 228 and an optical assembly 230 for optically determining fluid quality and/or other parameters. The electronic assembly 228 includes a printed circuit board (PCB) 229 with various electronic components mounted thereto, such as previously described (see FIG. 8 and related description) for applying voltage across the electrodes and processing resultant data from the electrodes for determining fluid parameters, as previously described.

The optical assembly 230 includes an optical body 232 located within a slot 234 formed in the flat wall section 226, a light source 238 such as a LED, positioned on the PCB for directing light into a light guide portion 240 of the optical body, and a light sensor 242, such as a two-dimensional imaging device, positioned for detecting the location, intensity, presence, and/or absence of light on an optical measurement surface 244 of the optical body 232. The optical measurement surface 244 is normally immersed in the fluid being measured and reflects and/or refracts the rays from the light source depending on the angle of the measurement surface, the angle of the light impinging on the measurement surface, and the refractive index of the fluid being measured. The light sensor 242 preferably comprises a two-dimensional array of sensors for capturing reflected rays and/or refracted rays from the light source 238. Further details of an exemplary optical assembly and its method of operation are described in U.S. Pat. No. 8,934,102 issued on Jan. 13, 2015 to Wirthlin et al., the disclosure of which is hereby incorporated by reference.

The top end cap 222 and bottom end cap 224 have circular grooves 246 and 248, respectively, that receive the ends of the electrodes 216, 218 and the impedance modifier 220 for retaining the components in position. Each end cap 222, 224 also includes an aperture 250, 252 that receives a hose connector 254 or the like so that fluid can be transported into and out of the reservoir 215. Although barbed connectors are shown at particular locations with respect to the housing, it will be understood that any type of connector or fitting can be used and that such connectors or fittings can be located at any position with respect to the housing so that fluid can continuously enter into the reservoir, circulate therethrough to surround the electrodes and impedance modifier 220, then exit the reservoir. In this manner, the volume between the electrodes are filled with the constant flow of fluid to be measured, so that measurement of the fluid and any changes thereto can be monitored during fluid flow.

The electrodes 216 and 218 are similar in construction with the exception of their particular size, and each includes a circular conductive plate with an electrically insulating coating, such as previously described with respect to FIG. 3. Insulative materials that may be suitable for the non-conductive layer can include, but are not limited to, Parylene, fluoropolymers, plastics, elastomers, enamels, ceramics, and so on, and that such materials may be applied using different techniques, such as painting, powder coating, dipping, vapor deposition, and so on, in different thicknesses depending on the particular liquid to be measured.

Moreover, some non-conductive materials may be more suitable then others for certain liquids to be measured. For automotive-type liquids, including DEF, antifreeze, windshield washer fluid, oil, and the like, it has been found that a thin coating, such as 0.5 to 1 Mil thickness of Parylene™ or other chemical vapor deposited poly(p-xylylene) polymers, is an especially suitable insulative layer for the liquid quality measurements as described above. However, it will be understood that other materials and/or material thickness can be used for the insulative layers without departing from the spirit and scope of the invention.

It will be further understood that in some instances the insulative layers may be eliminated, such as when the liquid is substantially non-conductive or when the electrodes are operatively associated with other components, such as a sacrificial anode, that is intended to bear the brunt of any potential galvanic corrosion, thereby reducing or eliminating degradation of the electrodes and thus subsequent degradation in the measurement of the liquid under consideration.

In accordance with a further embodiment of the invention, the insulative layers, when used, can be partially conductive, e.g. the layers need not be a perfect insulator, depending on the measuring techniques used for determining fluid properties.

A slot extends between opposite ends of each electrode, and the slot is also covered with the insulative layer for allowing the fluid to flow around both sides of the electrodes so that the effective plate area is doubled in size. This is especially advantageous where the size requirements are small. A connection tab 258 on the first electrode 216 and a connection tab 260 on the second electrode 218 extend through corresponding slots 262 and 264 formed in the top end cap 222 for connection to the PCB 229 via connectors 266 mounted on the PCB.

The impedance modifier 220 is constructed of an electrically insulative material and includes a generally circular-shaped side wall 270 with a thickness 272 (FIGS. 22 and 24) with axially extending outer flutes 274 and inner flutes 276 formed in the wall to reduce the thickness where not needed. One or more apertures 278 (only one shown in FIG. 24), extend through the thickness 272 of the wall 270 and function to impede the flow of electrons between the electrodes 216 and 218, to thereby increase the resistivity measurement of the fluid under consideration, as previously described, to thereby minimize capacitive effects of the electrodes and insulative layers so that at least substantially only the impedance of the fluid is measured. In this manner, inaccuracies that may otherwise occur due to the system components and their variations in manufacturing and environmental conditions can be substantially reduced or eliminated.

Referring now to FIGS. 25-29, a system 280 for measuring fluid properties, including fluid composition and quality for example, as well as other parameters, in accordance with yet another preferred embodiment of the invention is illustrated. The system 280 preferably includes multiple internal measuring surfaces for determining different fluid properties, including optic and impedance measuring surfaces that come in direct contact with the fluid. The system 280 can also ensure that the measuring surfaces will be free of foreign material that may skew the fluid measurement readings and thus lead to incorrect determination of the fluid properties.

The system 280 can be configured for inline, in-tank, or in-tank-head measurement systems to thereby measure the quality and/or type of a fluid as it is being transferred from one location to another, such as for example from a DEF tank to a catalytic converter or other part of a SCR system; from a filling station to the DEF tank; from the DEF tank and back into the DEF tank, and so on. A suitable in-tank-head approach that both determines the quality of fluid as it is withdrawn from a tank and the level of that same fluid within the tank is disclosed in U.S. application Ser. No. 14/677,914 filed on Apr. 2, 2015, the disclosure of which is hereby incorporated by reference.

The system 280 includes a housing assembly 282 with a first connector 284 and a second connector 286 extending therefrom for receiving tubing or the like to transport the fluid to be measured through the housing 282 and across the various surfaces located within the housing, as will be described below. The first and second connectors 282, 284 can serve either as fluid input or fluid output conduits with respect to the housing 282.

Figure 27:
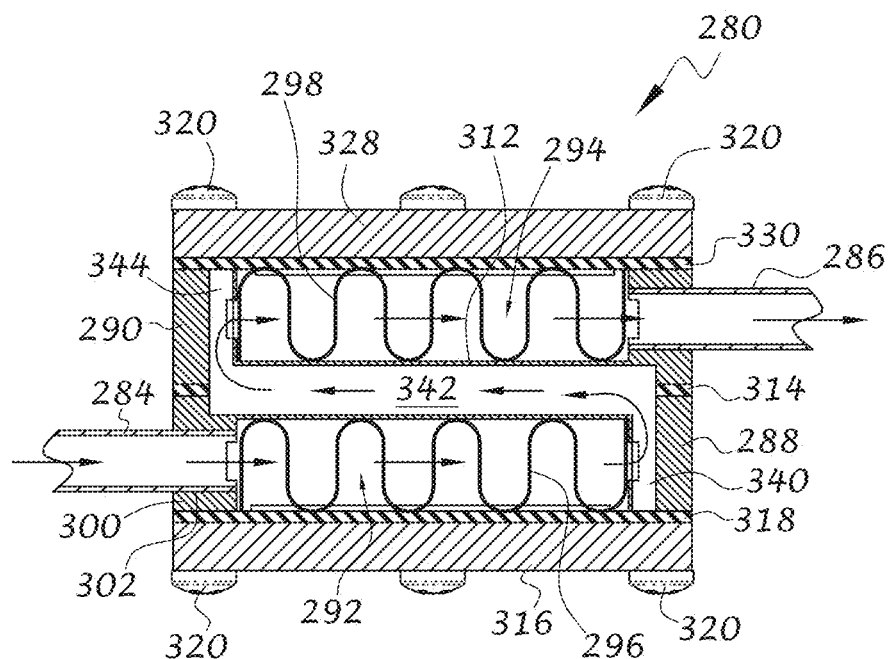
FIG. 27 is a sectional view thereof taken along line 27-27 of FIG. 26.
Figure 28:
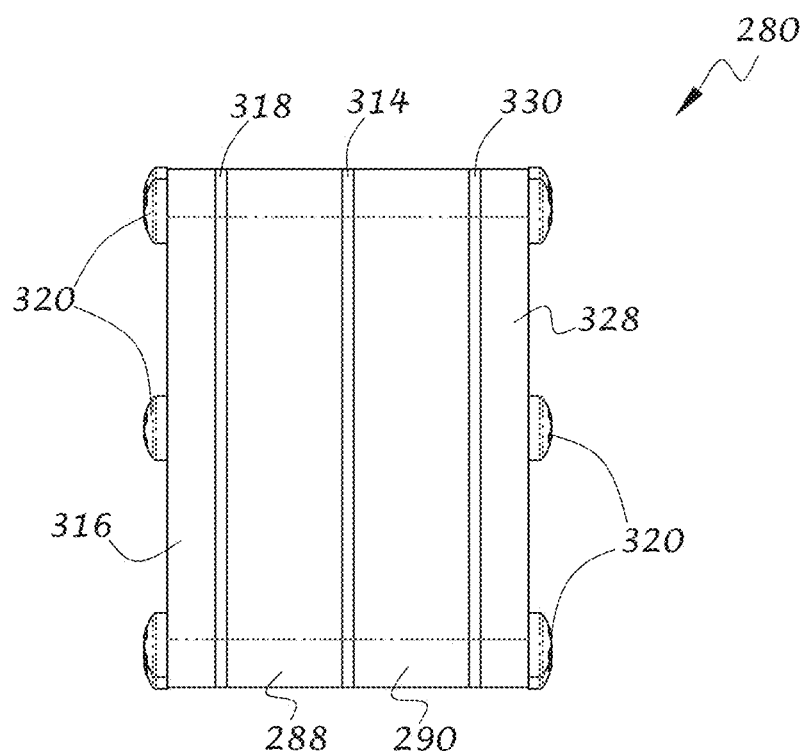
FIG. 28 is a left side elevational view thereof.
Figure 29:
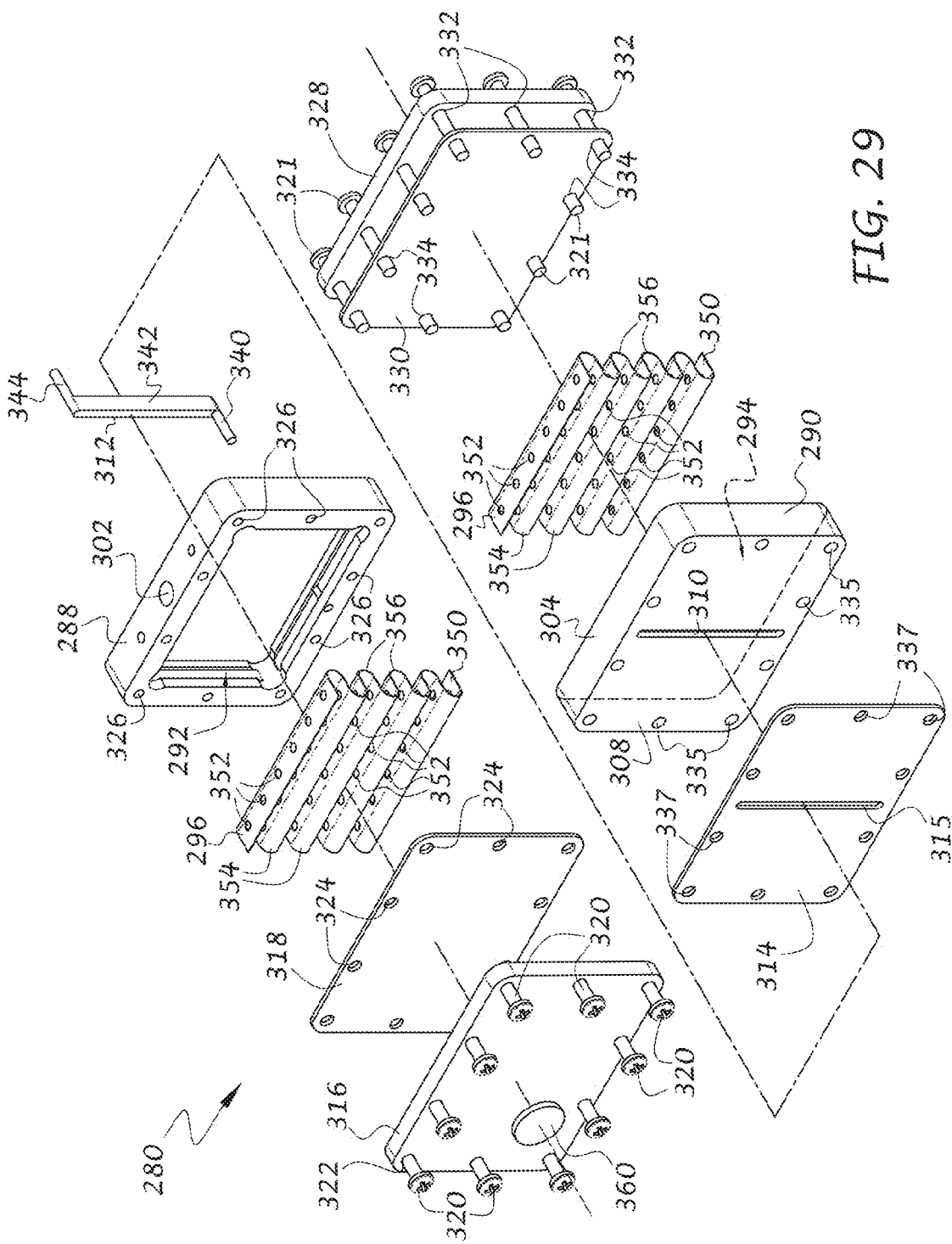
FIG. 29 is an exploded isometric view thereof showing similar principles of operation as the previous exemplary measurement systems of the invention.
Figure 30:
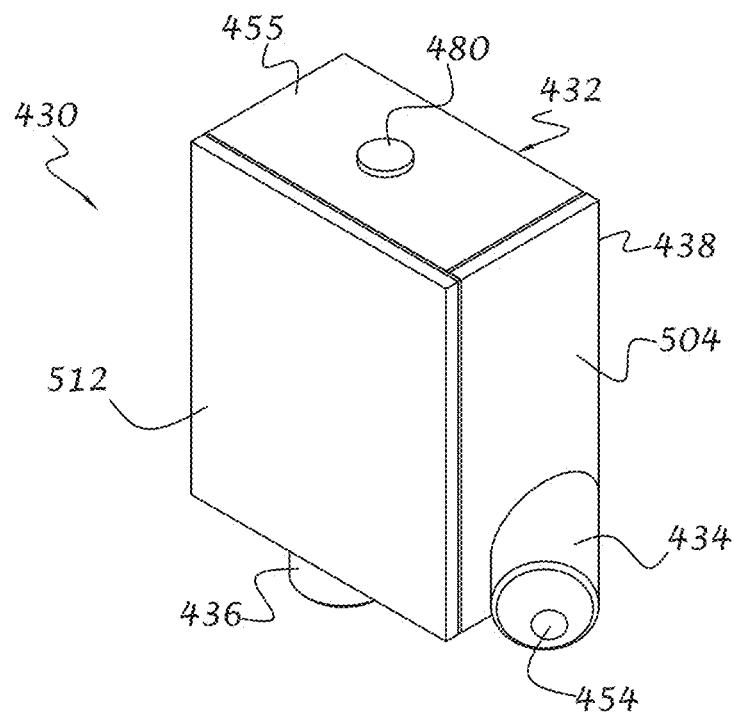
FIG. 30 is a rear isometric view of an exemplary measurement assembly in accordance with a further embodiment of the invention incorporating an optical sensor array, impedance measurement assembly, and cleaning module for minimizing or eliminating contamination on measuring surfaces that may affect the measurements.
Figure 31:
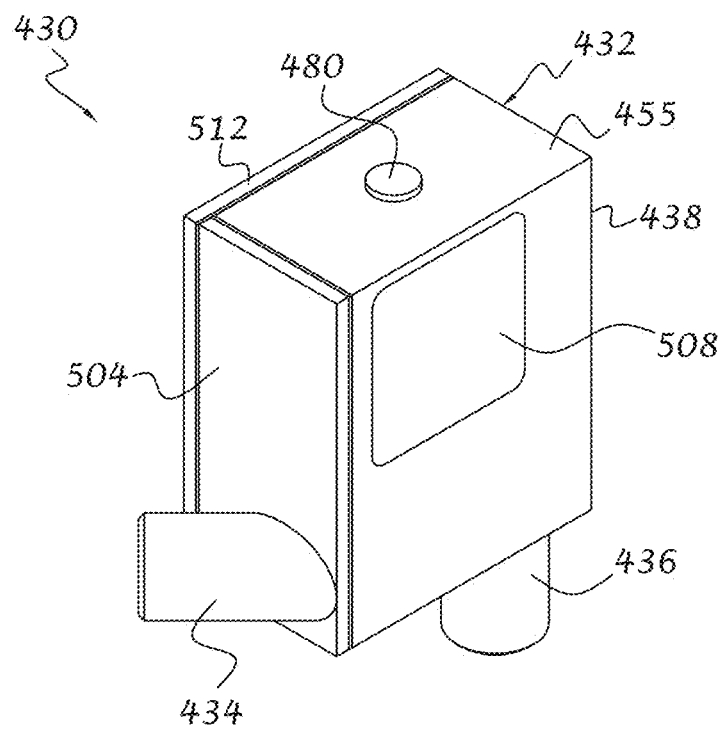
FIG. 31 is a front isometric view thereof.

As best shown in FIGS. 27 and 29, the housing assembly 282 has a first housing section 288 connected to a second housing section 290 to form respective first and second compartments or chambers 292, 294 for receiving respective first and second electrodes 296, 298 in a parallel orientation, i.e. the electrodes are in a side-by-side relationship in the adjacent compartments 292, 294. The first housing section 288 includes a continuous side wall 300 with an opening 302 formed in one side thereof for receiving the connector 284. Likewise, the second housing section 290 has a continuous wall 304 with an opening 306 (FIG. 27) formed in one side thereof for receiving the connector 286. The second housing section 290 also includes a bottom or rear wall 308 from which the side wall 304 extends. An elongate slot 310 is formed in the rear wall 308 and extends along a central portion thereof. An electrically insulative elongate impedance modifier 312 is positioned in the slot 310 between the compartments 292 and 294, and thus between the first and second electrodes 296, 298 respectively. The impedance modifier 312 is tubular in configuration to receive fluid as it travels between the compartments, and is thus located between the compartments to restrict the flow of electrical current between the electrodes 296 and 298, as with the previous embodiments. A gasket 314 is sandwiched between the housing sections 288, 290 and includes a centralized elongate slot 315 in alignment with the slot 310 to form a fluid-tight seal between the housing sections and between the rear wall 308 and the impedance modifier 312. In this manner, fluid can only travel between the compartments 292 and 294 via the impedance modifier 312.

A first end plate or cap 316 followed by a gasket 318 are connected to the first housing section 288 via fasteners 320 that extend through openings 322 in the first end plate 316, corresponding openings 324 in the gasket 318, and thread into corresponding openings 326 formed in the first housing section 288 to cover and seal the first compartment 292. Likewise, a second end plate or cap 328 followed by a gasket 330 are connected to the second housing section 290 via fasteners 321 that extend through openings 332 in the second end plate 328, corresponding openings 334 in the gasket 318, and corresponding openings 335 in the second housing section 290. The first and second housing sections 288, 290 are connected together via the fasteners 321 via corresponding openings 337 in the gasket 314, and thread into the corresponding openings 326 of the first housing section 288. In this manner, the first and second compartments are covered and sealed. The end plates can be removable for permitting access to the compartments 292, 294 for installation, removal, or service of the electrodes 296 and 298. It will be understood that other means for connecting and sealing the components together can be used without departing from the spirit and scope of the invention.

The impedance modifier 312 has a first conduit section 340, a second conduit section 342, and a third conduit section 344, with the first conduit section located in the first compartment 292, the second conduit section located between the first and second compartments, and the third conduit section located in the second compartment 294. Since fluid is only allowed to flow between the compartments through the impedance modifier 312, the fluid to be measured can continuously flow into the housing assembly and fill the first and second compartments for measuring the fluid properties before exiting the housing assembly 282. Once the fluid is measured, it exits the housing assembly and can be directed to a tank that holds the fluid, a catalytic converter in a SCR system, or other system or component(s) of the vehicle or machine that utilizes the fluid.

The impedance modifier 312 is of a particular diameter or cross dimension and the length of the impedance modifier as defined by the conduit sections, establish a restricted flow space or volume through which the fluid, and thus the electrons associated with the fluid, must travel between the electrodes 296 and 298. It will be understood that the impedance modifier 312 can include more than one restrictor, a single conduit extending between the electrode compartments, and can be of any suitable shape, size, and length depending on the fluid and the fluid properties to be measured.

The electrodes 296, 298 are identical in construction and each includes a conductive plate 350 with holes 352 formed therein to allow fluid in the compartments 292, 294 to flow through the electrodes and expose opposing surfaces of the electrodes so that the fluid within the compartments are in contact with the opposing surfaces to thereby maximize the surface area of the electrodes in a minimum amount of space. To that end, each electrode 296, 298 can be shaped to maximize surface area. By way of example, each plate can be corrugated in shape with parallel, alternating ridges 354 and valleys 356 to enable more electrode material, and thus surface area, to fit within the compartments 292, 294. It will be understood that the electrodes can be formed of any suitable shape and size.

Each conductive plate is preferably coated with an electrically non-conductive layer (not shown) on opposing sides thereof and through the holes 352 so that the conductive plate is isolated from the liquid within the compartments. In this manner, corrosion of the electrodes as well as their consequent electrical signal degradation are substantially reduced or eliminated. Insulative materials that may be suitable for the non-conductive layer can include, but are not limited to, Parylene, fluoropolymers, plastics, elastomers, enamels, ceramics, and so on, and that such materials may be applied using different techniques, such as painting, powder coating, dipping, vapor deposition, and so on, in different thicknesses depending on the particular liquid to be measured.

Moreover, some non-conductive materials may be more suitable then others for certain liquids to be measured. For automotive-type liquids, including DEF, antifreeze, windshield washer fluid, oil, and the like, it has been found that a thin coating, such as 0.5 to 1 Mil thickness of Parylene™ or other chemical vapor deposited poly(p-xylylene) polymers, is an especially suitable insulative layer for the liquid quality measurements as described above. However, it will be understood that other materials and/or material thickness can be used for the insulative layers without departing from the spirit and scope of the invention.

It will be further understood that in some instances the insulative layers may be eliminated, such as when the liquid is substantially non-conductive or when the electrodes are operatively associated with other components, such as a sacrificial anode, that is intended to bear the brunt of any potential galvanic corrosion, thereby reducing or eliminating degradation of the electrodes and thus subsequent degradation in the measurement of the liquid under consideration.

In accordance with a further embodiment of the invention, the insulative layers, when used, can be partially conductive, e.g. the layers need not be a perfect insulator, depending on the measuring techniques used for determining fluid properties.

Due to the configuration of the insulated plates, their relative position, and the fluid flow therebetween, a series RC network is created that minimizes plate capacitance and maximizes measurement of impedance through the fluid. Using a large area capacitive plate to provide non-electrical contact with the fluid causes an additional RC network, or impedance to be interjected, while minimizing the RC network of the plates and insulative coating. As the plate size is increased, so is the effective cross section of the fluid. Thus, the ratio of the capacitors (plate insulation and fluid capacitance) is relatively constant. In order to maximize accuracy of the fluid measurement, the effect of plate capacitance is minimized by increasing the spacing between the plates to lower the fluid dielectric constant, as well as creating one or more impedance modifiers to reduce the cross section of the fluid. Where space constraints between the plates become a concern, it is possible to achieve similar results by further restricting fluid flow between the plates. Hence, the impedance modifiers can vary in size and number to accommodate a particular plate configuration. Accordingly, accuracy of the impedance measurement of the fluid is greatly increased and the system of the invention is capable of differentiating different fluids and mixtures of different fluids, as demonstrated above, with relatively high accuracy.

However, even with the accuracy greatly increased over prior art impedance measurement techniques, there still remains the possibility that contaminants, films, particles, or any other undesirable material, will collect on the measuring surfaces of the electrodes, and change the plate impedance, which may have an undesirable effect on measuring the impedance of the fluid. In many real-world scenarios, it is impractical to remove the plates for cleaning due to the inaccessibility of the electrodes. Even when the electrodes are accessible, the service intervals to clean the measuring surfaces of the electrodes may be impractical. It has been observed that contaminants may almost immediately begin to collect on the electrodes and fluid measurements can quickly become skewed. Accordingly, the potentially high accuracy of the impedance measurements of the invention can be affected over varying amounts of time without a way to continuously or intermittently clean the measuring surfaces. The same holds true for the optical measuring surface 244 (FIG. 23) of the optical measurement assembly 230 previously described.

Figure 25:
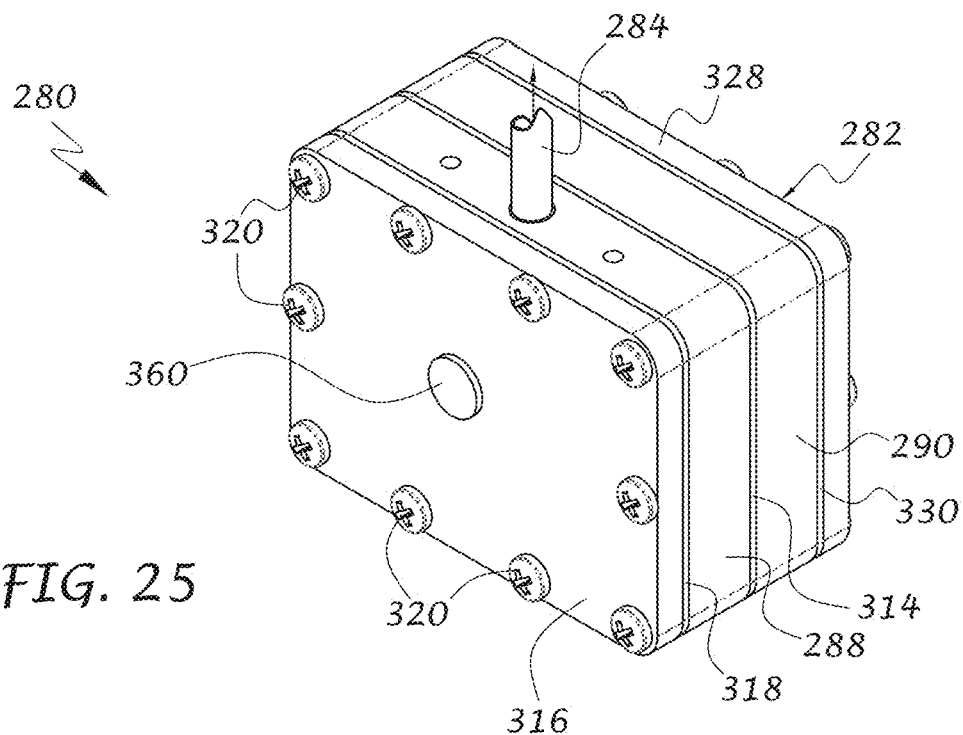
FIG. 25 is an isometric view of a measurement system for determining fluid quality and other parameters in accordance with yet a further exemplary embodiment of the present invention.
Figure 26:
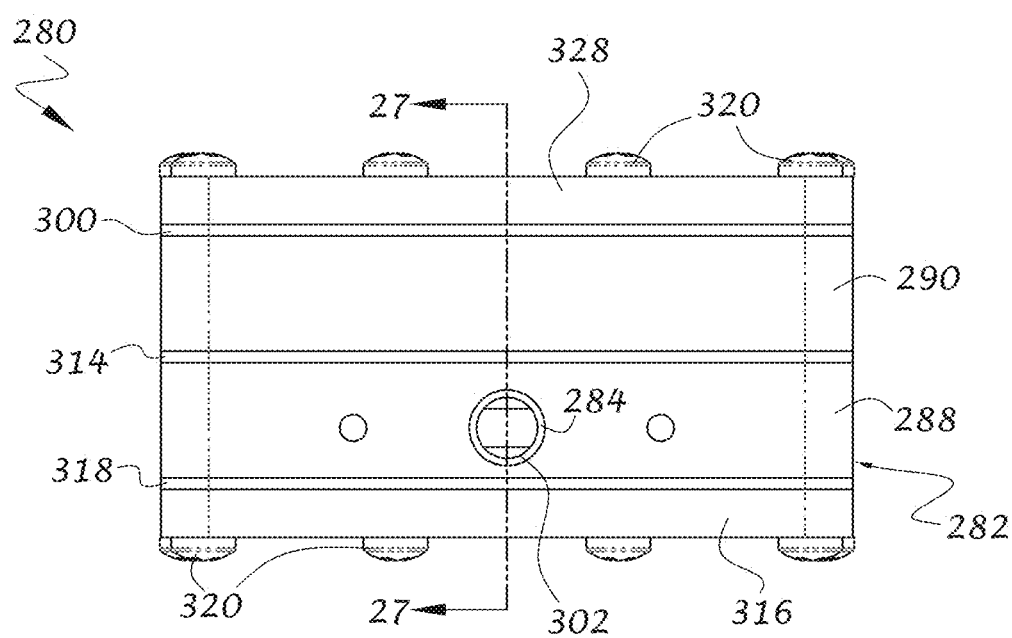
FIG. 26 is a top plan view thereof.

Therefore, as shown in FIGS. 25 and 29, a cleaning device 360 can be positioned on one or more of the end plates 316, 328 or any other suitable location and/or orientation with respect to the housing assembly. The cleaning device 360 generates ultrasonic waves in the fluid being measured for cleaning the measuring surface of the electrodes 296 and 298, as well as other surfaces on which contaminants may collect, under the principles as disclosed in U.S. application Ser. No. 14/722,116 filed on May 26, 2015, the disclosure of which is hereby incorporated by reference. The transducer 360 can be constructed of piezoelectric or magnetostrictive materials that vibrate at a predetermined frequency, discrete frequency steps, and/or sweeping frequencies in the ultrasonic bandwidth.

In use, the one or more transducers are placed at one or more locations on or in the housing assembly and/or other locations where the fluid is subjected to ultrasonic vibration so that particles, contaminants, film, layers, and the like that may tend to collect on, or be in the process of collecting on, the measuring surfaces can be cleaned ultrasonically during fluid flow, when the fluid is stopped, or at any other convenient time for cleaning or ensuring the cleanliness of the measuring surfaces. It will be understood that other cleaning devices can be used without departing from the spirit and scope of the invention. The fluid being measured also conveniently functions as the cleaning fluid to prevent, substantially reduce, or eliminate film formation on the measuring surfaces.

During the cleaning operation, fluid properties can continue to be monitored. Detecting changes or differences in fluid properties at the commencement of the cleaning operation would suggest that the cleaning is effective, while stabilization of the fluid properties at some point after commencement of the cleaning process would suggest that cleaning of the measuring surfaces has completed.

In accordance with a further embodiment of the invention, a separate reservoir of cleaning fluid (not shown) can be provided. In this instance, when the cleaning operation is commenced, the flow of fluid being measured would be terminated and the flow of cleaning fluid would commence to flush out contaminants while operating the cleaning device 360. When the cleaning operation has finished, the flow of fluid being measured would then recommence and the flow of cleaning fluid would be terminated.

Referring now to FIGS. 30-33, a system 430 for measuring fluid properties, including fluid composition and quality for example, as well as other parameters, in accordance with yet another preferred embodiment of the invention is illustrated. The system 430 preferably includes multiple internal measuring surfaces for determining different fluid properties, including optic and impedance measuring surfaces that come in direct contact with the fluid. The system 430 ensures that the measuring surfaces will be free of foreign material that may skew the fluid measurement readings and thus lead to incorrect determination of the fluid properties.

Although the system 430 will be described in the context of optical and impedance measuring surfaces to facilitate description of the invention, it will be understood that the invention is not limited thereto, as the structure and methods disclosed herein may be applied to any measuring surface that may come in contact with the fluid being measured using virtually any measurement technology, so that accumulation of foreign material on such surfaces is prevented, substantially reduced, or eliminated. Such surfaces may include, but are not limited to, optical lenses, filters, prisms, conduits, plates, and so on, related to optical fluid measurement, liquid level detection, and so on; capacitive electrodes for determining liquid level and/or fluid properties, tuning fork surfaces for determining liquid level and/or fluid properties, resistance wires, plates, and coils used in liquid level measurement, and so on.

The system 430 can be configured for inline, in-tank, or in-tank-head measurement systems to thereby measure the quality and/or type of a fluid as it is being transferred from one location to another, such as for example from a DEF tank to a catalytic converter or other part of a SCR system; from a filling station to the DEF tank; from the DEF tank and back into the DEF tank, and so on, as described and incorporated by reference above.

The system 430 includes a housing 432 with a first connector 434 and a second connector 436 extending therefrom for receiving tubing or the like to transport the fluid to be measured through the housing 432 and across the various measuring surfaces located within the housing, as will be described below. The first and second connectors 434, 436 can serve either as fluid input or fluid output conduits with respect to the housing 432.

Figure 32:
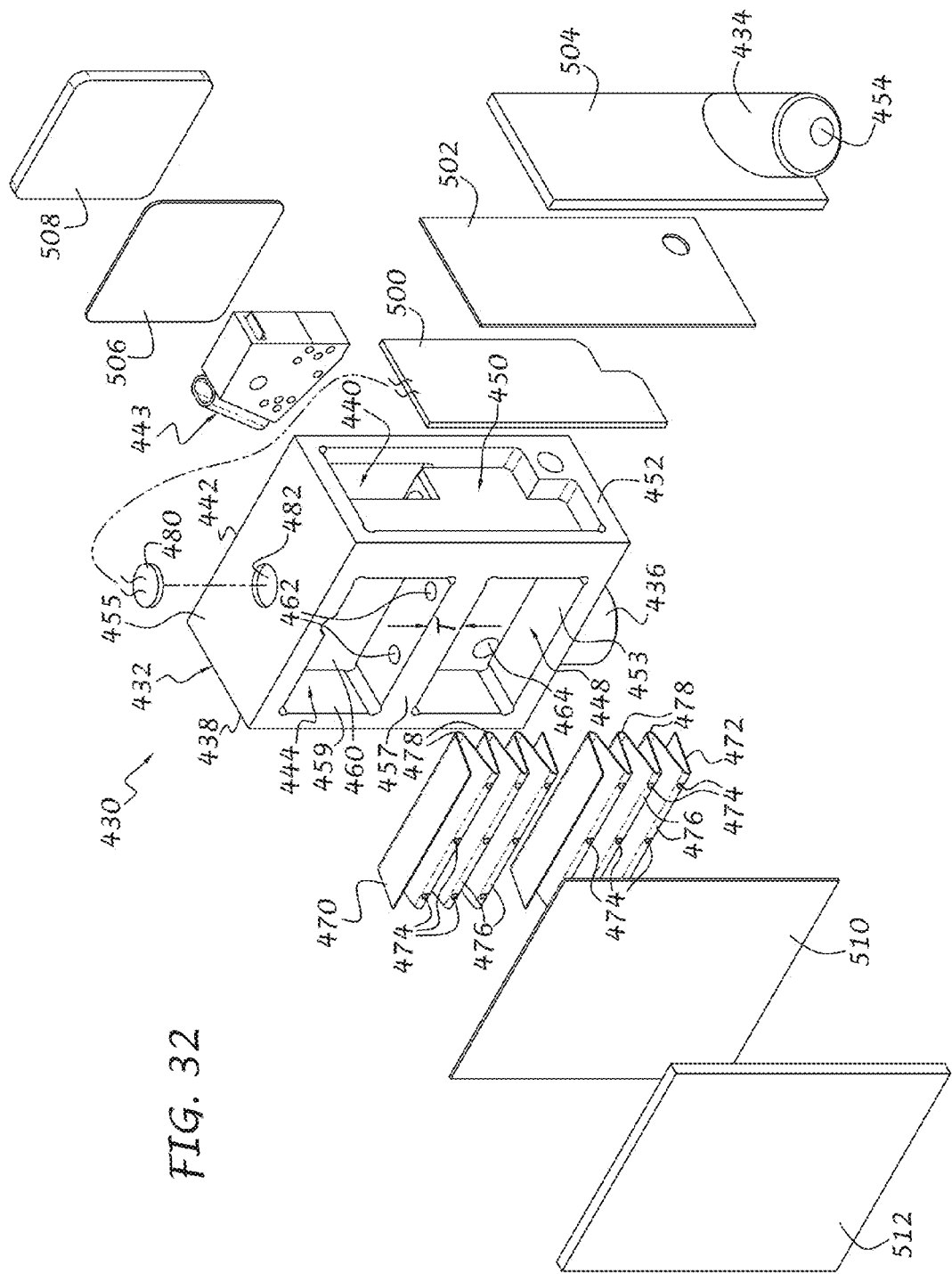
FIG. 32 is a rear exploded isometric view thereof.
Figure 33:
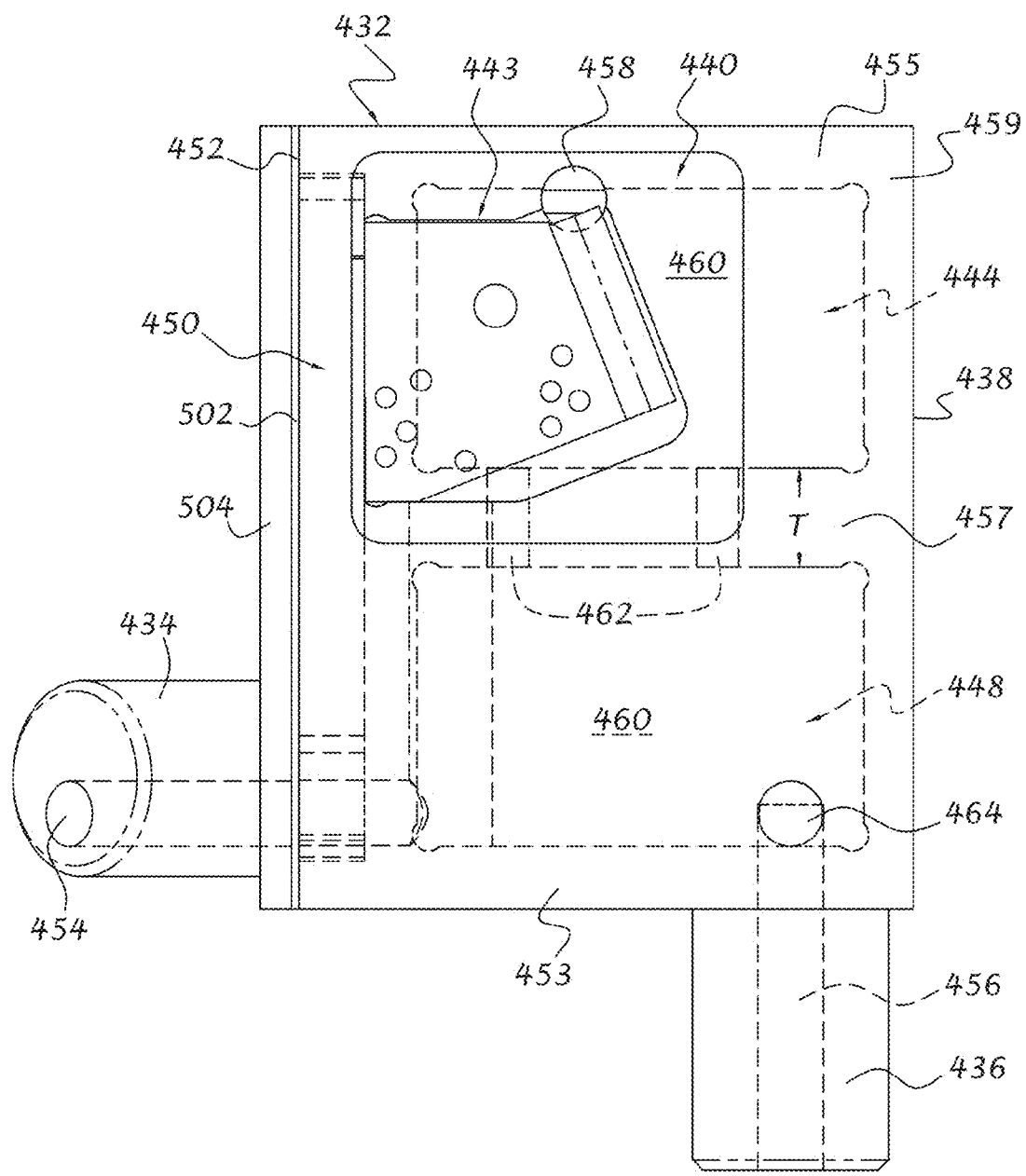
FIG. 33 is a front elevational view of a housing that forms part of the measurement assembly of FIG. 30 and showing hidden features of the housing in dashed line together with a representative optical component of the invention.

As best shown in FIGS. 32 and 33, the housing 432 includes a first compartment or chamber 440 formed in a front wall 442 thereof for receiving an optical measurement assembly, such as described in U.S. Pat. No. 8,934,102 previously incorporated by reference, a second compartment or chamber 444 formed in a rear wall 446 of the housing 438, a third compartment or chamber 448 formed in the rear wall 446 below the second compartment 444, and a fourth compartment or chamber 450 formed in a side wall 452 of the housing 432. The first compartment 440 is in fluid communication with the first connector 434 via a first conduit 454 formed therein while the third compartment 448 is in fluid communication with the second connector 436 via a second conduit 456 formed therein. The first compartment 440 and second and third compartments 444, 448 are separated by a first internal dividing wall 460 that extends between a lower wall 453 and an upper wall 455 of the housing 432. Likewise, the second and third compartments 444, 448 are separated from each other by a second internal dividing wall 457 that extends between the side wall 452 and an opposite side wall 459 of the housing 432. The first and second compartments 440, 444 are in fluid communication with each other via a first bore 458 that extends through the first internal wall 460. Likewise, the second and third compartments 444, 448 are in fluid communication with each other via one or more impedance modifiers 462, embodied as a pair of second bores that extend through the second internal wall 457 between the second and third compartments. The second and third compartments are arranged in a stacked, end-to-end relationship in this embodiment, whereas in the previous embodiment the compartments containing the electrodes are arranged in a parallel side by side relationship. Finally, the third compartment 448 is in fluid communication with the second conduit 456 via a third bore 464 that extends through the first internal wall 460 at a location spaced from the first compartment 440. In this manner, the fluid to be measured can continuously flow through and fill the first, second, and third compartments for measuring the fluid properties before exiting the housing 432. Once the fluid is measured, it exits the housing and can be directed to a tank that holds the fluid, a catalytic converter in a SCR system, or other system or component(s) of the vehicle or machine that utilizes the fluid.

The first compartment 440 is configured to receive an optical measurement assembly 443 for optically monitoring the properties of the fluid in the housing 438, as described in previous embodiments and previously incorporated by reference, which includes the first signal generating device in the form of an optical array. The second and third compartments 444 and 448 are configured to receive electrodes 470 and 472, respectively, which form part of a second signal generating device for measuring the impedance of the fluid. The second intermediate wall 457 has a thickness "T" that defines the spacing or distance between the electrodes 470 and 472. The one or more impedance modifiers 462 are of a particular diameter or cross dimension and the length of the impedance modifiers 462 as defined by the wall thickness T, establish a restricted flow space or volume through which the fluid, and thus the electrons associated with the fluid, must travel between the electrodes 470 and 472. It will be understood that the impedance modifiers 462 can include a single bore or more than two bores, and can be of any suitable shape, size, and length depending on the fluid and the fluid properties to be measured.

As best shown in FIG. 32, each of the electrodes 470 and 472 include a conductive plate with holes 474 formed therein to allow fluid in the compartments 444, 448 to flow through the electrodes and expose opposing surfaces of the electrodes so that the fluid within the compartments 444, 448 can flow through the electrodes to thereby maximize the surface area of the electrodes in a minimum amount of space. To that end, each electrode 470, 472 can be shaped to maximize surface area. By way of example, each plate can be formed with parallel, alternating ridges 476 and valleys 478 to enable more electrode material, and thus surface area, to fit within the compartments 444, 448. It will be understood that the electrodes can be formed of any suitable shape and size.

Each conductive plate is preferably coated with an electrically non-conductive layer (not shown) on opposing sides thereof and through the holes 476 so that the conductive plate is isolated from the liquid within the compartments. In this manner, corrosion of the electrodes as well as their consequent electrical signal degradation are substantially reduced or eliminated. Insulative materials that may be suitable for the non-conductive layer can include, but are not limited to, Parylene, fluoropolymers, plastics, elastomers, enamels, ceramics, and so on, and that such materials may be applied using different techniques, such as painting, powder coating, dipping, vapor deposition, and so on, in different thicknesses depending on the particular liquid to be measured.

Moreover, some non-conductive materials may be more suitable then others for certain liquids to be measured. For automotive-type liquids, including DEF, antifreeze, windshield washer fluid, oil, and the like, it has been found that a thin coating, such as 0.5 to 1 Mil thickness of Parylene™ or other chemical vapor deposited poly(p-xylylene) polymers, is an especially suitable insulative layer for the liquid quality measurements that will be described in greater detail below. However, it will be understood that other materials and/or material thickness can be used for the insulative layers without departing from the spirit and scope of the invention.

It will be further understood that in some instances the insulative layers may be eliminated, such as when the liquid is substantially non-conductive or when the electrodes are operatively associated with other components, such as a sacrificial anode, that is intended to bear the brunt of any potential galvanic corrosion, thereby reducing or eliminating degradation of the electrodes and thus subsequent degradation in the measurement of the liquid under consideration.

In accordance with a further embodiment of the invention, the insulative layers, when used, can be partially conductive, e.g. the layers need not be a perfect insulator, depending on the measuring techniques used for determining fluid properties.

Due to the configuration of the insulated plates, their relative position, and the fluid flow therebetween, a series RC network is created that minimizes plate capacitance and maximizes measurement of impedance through the fluid. Using a large area capacitive plate to provide non-electrical contact with the fluid causes an additional RC network, or impedance to be interjected, while minimizing the RC network of the plates and insulative coating. As the plate size is increased, so is the effective cross section of the fluid. Thus, the ratio of the capacitors (plate insulation and fluid capacitance) is relatively constant. In order to maximize accuracy of the fluid measurement, the effect of plate capacitance is minimized by increasing the spacing between the plates to lower the fluid dielectric constant, as well as creating the impedance modifiers 462 to reduce the cross section of the fluid. Where space constraints between the plates become a concern, it is possible to achieve similar results by further restricting fluid flow between the plates. Hence, the impedance modifiers can vary in size and number to accommodate a particular plate configuration. Accordingly, accuracy of the impedance measurement of the fluid is greatly increased and the system of the invention is capable of differentiating different fluids in a mixture of fluids with relatively high accuracy.

However, even with the accuracy greatly increased over prior art impedance measurement techniques, there still remains the possibility that contaminants, films, particles, or any other undesirable material, will collect on the measuring surfaces of the electrodes, and change the plate impedance, which may have an undesirable effect on measuring the impedance of the fluid. In many real-world scenarios, it is impractical to remove the plates for cleaning due to the inaccessibility of the electrodes. Even when the electrodes are accessible, the service intervals to clean the measuring surfaces of the electrodes may be impractical. It has been observed that contaminants may almost immediately begin to collect on the electrodes and fluid measurements can quickly become skewed.

Accordingly, the potentially high accuracy of the impedance measurements of the invention can be affected over varying amounts of time without a way to continuously or intermittently clean the measuring surfaces. The same holds true for the optical measuring surface of the optical measurement assembly 443 (FIG. 32) previously described.

Therefore, in accordance with the invention, and as shown in FIG. 32, a cleaning device 480 is positioned within a depression 482 formed in the upper wall 455 of the housing 438 at one or more locations and/or orientations with respect to the housing. The cleaning device 480 may additionally or alternately be positioned on other wall surfaces without departing from the spirit and scope of the invention. Although the wall 455 is shown as integral with the housing 438, the wall can comprise a sheet of suitable material mounted over an opening in the housing and to which the cleaning device 480 is attached. The cleaning device 480 generates ultrasonic waves in the fluid being measured for cleaning the measuring surface of the optical assembly 443 and the measuring surfaces of the electrodes 470 and 472, as well as other surfaces on which contaminants may collect, under the principles as previously described. The transducer 480 can be constructed of piezoelectric or magnetostrictive materials that vibrate at a predetermined frequency, discrete frequency steps, and/or sweeping frequencies in the ultrasonic bandwidth.

In use, the one or more transducers placed at one or more locations on or in the housing 438 and/or other locations where the fluid is subjected to ultrasonic vibration so that particles, contaminants, film, layers, and the like that may tend to collect on, or be in the process of collecting on, the measuring surfaces can be cleaned ultrasonically during fluid flow, when the fluid is stopped, or at any other convenient time for cleaning or ensuring the cleanliness of the measuring surfaces. It will be understood that other cleaning devices can be used without departing from the spirit and scope of the invention. As in the previous embodiments, the fluid being measured also functions as the cleaning fluid to prevent, substantially reduce, or eliminate film formation on the measuring surfaces.

During the cleaning operation, fluid properties can continue to be monitored. Detecting differences in fluid properties at the commencement of the cleaning operation would suggest that the cleaning is effective, while stabilization of the fluid properties at some point after commencement of the cleaning process would suggest that cleaning of the measuring surfaces has completed.

In accordance with a further embodiment of the invention, a separate reservoir of cleaning fluid (not shown) can be provided. In this instance, when the cleaning operation is commenced, the flow of fluid being measured would be terminated and the flow of cleaning fluid would commence to flush out contaminants while operating the cleaning device 480. When the cleaning operation has finished, the flow of fluid being measured would then recommence and the flow of cleaning fluid would be terminated.

The system 430 for measuring fluid properties also includes a printed circuit board (PCB) 500 positioned in the fourth compartment 450 of the housing 438, followed by a side gasket 502 and a side cover 504, which are in turn connected to or integrally formed with the connector 434, to seal the PCB within the housing and isolate it from the fluid flow through the housing. The PCB is similar in construction to the PCB previously described, with the exception that interface circuitry (not shown) for injecting a frequency or series of frequencies, and/or an electrical pulse at one or more amplitudes across the electrodes via processor control, as well as appropriate circuitry for measuring the impedance of the fluid between the electrodes in response to the injected frequencies and/or electrical pulse(s), can be associated with the PCB and/or the controller. The provision of the side cover 504 facilitates access to the PCB for installation, servicing, or replacement.

The optical measurement assembly 443 is positioned in the second compartment 440, followed by a front gasket 506 and a front cover 508 to seal the optical measurement assembly within the housing. The provision of the front cover 508 and gasket 506 facilitates installation and removal of the optical measurement assembly 443 with respect to the housing 438.

A rear gasket 510 followed by a rear cover 512 are connected to the housing 438 and covers the compartments 444 and 448, and the electrodes located therein. Again, the provision of the rear cover 512 permits access to the compartments 444 and 448 for installation, removal, or service of the electrodes 470 and 472.

The techniques and methods discussed herein and as defined by the appended claims can be implemented in digital electronic circuitry, or in computer hardware, firmware, software, or combinations thereof. The techniques and methods of the invention may be implemented in a computer program product tangibly embodied in a machine-readable storage device for execution by a programmable processor; and the methods described herein may be performed by a programmable processor executing a program of instructions to perform functions by operating on input data and generating output. Further embodiments may advantageously be implemented in one or more computer programs that are executable on a programmable system including at least one programmable processor coupled to receive data and instructions from and transmit data and instructions to a data storage system, at least one input device, and at least one output device. Each computer program may be implemented in a high level procedural or object-oriented programming language, or in assembly or machine language, which can be compiled or interpreted. Suitable processors include, by way of example, both general and special purpose microprocessors. Generally, a processor receives instructions and data from read-only memory and/or RAM. Storage devices suitable for tangibly embodying computer program instructions and data include all forms of non-volatile memory including, by way of example and not by limitation, semiconductor memory devices, such as EPROM, EEPROM, and flash memory devices; magnetic disks such as internal hard disks and removable disks; magneto-optical disks; CD-ROM disks; solid state drives, and so on. Any of the foregoing may be supplemented by, or incorporated in, specially designed application specific integrated circuits (ASICs).

It will be understood that measurement of the DEF and the particular results obtained are by way of example only, since it is anticipated that substantially any fluid (including but not limited to gases, liquids, and solutions) and solid materials can be measured through the systems and methods of the present invention.

It will be understood that the above-described embodiments can be permanently mounted on equipment or may be constructed as portable units for measuring the properties of a variety of different fluids within transport lines, tanks or containers, across many industries, by users, field technicians, maintenance workers, claims adjusters, and so on.

It will be understood that terms of orientation and/or position as used throughout the invention relate to relative rather than absolute orientations and/or positions.

It will be appreciated by those skilled in the art that changes could be made to the embodiments described above without departing from the broad inventive concept thereof. It will be understood, therefore, that this invention is not limited to the particular embodiments disclosed, but it is intended to cover modifications within the spirit and scope of the present invention as defined by the appended claims.

We claim:

1. A system for measuring at least one property of a fluid, the system comprising:
   a housing for receiving the fluid, the housing having a first chamber with a first volume and a second chamber with a second volume;
   an impedance modifier separating the first and second chambers;
   a first electrode positioned in the first chamber of the housing, the first electrode having a first electrically conductive plate, a relatively large first surface area with respect to the first chamber, and a first electrically insulative coating positioned on the first plate for electrically isolating the first plate from the fluid, the first coating being relatively thin with respect to a thickness of the first plate, with the relatively large first surface area of the first plate and the relatively thin first coating together with the fluid in contact with the first coating create a first capacitance that is substantially negligible with respect to an impedance of the fluid;

a second electrode positioned in the second chamber of the housing and spaced from the first electrode, the second electrode having a second electrically conductive plate, a relatively large second surface area with respect to the second chamber, and a second electrically insulative coating positioned on the second plate for electrically isolating the second plate from the fluid, the second coating being relatively thin with respect to a thickness of the second plate, with the relatively large second surface area of the second plate and the relatively thin second coating together with the fluid in contact with the second coating create a second capacitance that is substantially negligible with respect to the impedance of the fluid;

the impedance modifier including at least one opening or conduit with a predetermined diameter or cross-dimension and a predetermined length to define a third volume that is less than the first and second volumes and creating a reduced flow volume so that electrons associated with the fluid are forced to funnel through the reduced flow volume between the first and second electrodes to thereby increase the impedance of the fluid between the first and second electrodes; and electronic circuitry operably associated with the first and second electrodes for generating signals across the electrodes and the fluid located between the electrodes, and analyzing resulting signals to determine the one or more properties of the fluid.

2. A system according to claim 1, wherein the electronic circuitry includes a signal generating module for generating a plurality of different waveform voltages across the first and second electrodes.

3. A system according to claim 2, wherein the plurality of different waveform voltages comprise sinusoidal waveforms at different frequencies.

4. A system according to claim 3, wherein the signal generator applies the plurality of different frequencies across the electrodes sequentially.

5. A system according to claim 3, wherein the signal generator applies the plurality of different frequencies across the electrodes simultaneously in a pulse waveform that comprises the plurality of different frequencies.

6. A system according to claim 3, and further comprising a processor for receiving data associated with a change in impedance of the fluid at the plurality of different frequencies such that a different impedance value is generated with each frequency, and generating a unique footprint for the fluid based on each impedance value at each of the plurality of different frequencies.

7. A system according to claim 6, and further comprising a memory for storing a plurality of different footprints associated with a plurality of different known fluids.

8. A system according to claim 7, wherein the processor is configured to receive data associated with a change in impedance from an unknown fluid at the plurality of different frequencies such that a different impedance value is generated at each frequency, generating a unique footprint for the unknown fluid based on each impedance value at each of the plurality of different frequencies, and identifying the unknown fluid by comparing the unique footprint of the unknown fluid with one or more unique footprints of the known fluids.

9. A system according to claim 1, wherein each of the first and second conductive plates comprises opposite faces and an edge located between the faces, the conductive plate being configured so that the opposite faces are immersed in the fluid.

10. A system according to claim 9, wherein each conductive plate comprises at least one plate opening extending between the opposite faces so that fluid flows through the at least one plate opening and surrounds the opposite faces, thereby approximately doubling a surface area of each electrode within its respective chamber.

11. A system according to claim 10, wherein the insulative layer surrounds the conductive plate, the edge, and the at least one opening to substantially reduce or eliminate corrosion of the electrodes in the presence of fluid.

12. A system according to claim 11, wherein the impedance modifier comprises:

a divider wall extending between the first and second chambers to limit fluid flow and electron flow between the first and second electrodes; and the at least one opening or conduit extending through the divider wall in fluid communication with the first and second chambers.

13. A system according to claim 1, wherein the first and second chambers are oriented in a side-by-side relationship.

14. A system according to claim 1, wherein the first and second chambers are oriented in an end-to-end relationship.

15. A system according to claim 12, wherein the conductive plates are circular in shape, and are positioned coaxial, with the first conductive plate located with the second conductive plate, and the divider wall located between the first and second electrodes.

16. A system according to claim 11, wherein the first and second conductive plates are corrugated in shape to further increase the surface area thereof.

17. A method for measuring at least one property of a fluid, the method comprising:

providing a housing with first and second chambers;

providing an impedance modifier between the first and second chambers such that fluid flows between the first and second chambers through the impedance modifier;

providing first and second conductive electrodes within the first and second chambers, respectively;

flowing the fluid to be measured across the first electrode, through the impedance modifier, and across the second electrode such that a flow of electrons associated with the fluid through the impedance modifier are impeded, thereby increasing the impedance of the fluid;

substantially reducing a first capacitance associated with the first electrode and a second capacitance associated with the second electrode such that only the fluid to be measured is at least substantially monitored;

generating a plurality of different waveform voltages across the first and second electrodes and the fluid within the impedance modifier;

monitoring an output thereof to thereby obtain data related to an impedance value of the fluid for each generated waveform voltage with a different impedance value being generated at each waveform voltage; and combining data related to the output of the waveform voltages to create a unique identification signature for the fluid.

18. A method according to claim 17, wherein the plurality of different waveform voltages comprise sinusoidal waveforms at different frequencies.

19. A method according to claim 18, wherein the plurality of different frequencies are applied across the electrodes sequentially.

20. A method according to claim 19, wherein the plurality of different frequencies are applied across the electrodes simultaneously in a pulse waveform that comprises the plurality of different frequencies.

21. A method according to claim 17, and further comprising generating and storing a plurality of different unique identification signatures associated with a plurality of different known fluids.

22. A method according to claim 21, and further comprising:
generating a unique identification signature for an unknown fluid; and
identifying the unknown fluid by comparing the unique identification signature of the unknown fluid with one or more unique identification signatures of the known fluids.

23. A method according to claim 17, wherein the step of substantially reducing the first capacitance associated with the first electrode and the second capacitance associated with the second electrode comprises providing each electrode with a relatively large first surface area with respect to the chamber, and applying an electrically insulative coating on the plate for electrically isolating the plate from the fluid, the coating being relatively thin with respect to a thickness of the plate, with the relatively large first surface area of the plate and the relatively thin first coating together with the fluid in contact with the coating creating a capacitance that is substantially negligible with respect to the impedance value of the fluid.

* * * * *